(12) United States Patent
Aguirre et al.

(10) Patent No.: US 7,312,037 B2
(45) Date of Patent: Dec. 25, 2007

(54) IDENTIFICATION OF THE GENE AND MUTATION RESPONSIBLE FOR PROGRESSIVE ROD-CONE DEGENERATION IN DOG AND A METHOD FOR TESTING SAME

(75) Inventors: Gustavo Aguirre, Philadelphia, PA (US); Gregory M. Acland, Kennett Square, PA (US); Barbara Zangerl, Philadelphia, PA (US); Orly Goldstein, Ithaca, NY (US); Susan Pearce-Kelling, Berkshire, NY (US); Jeanette S. Felix, Horseheads, NY (US); Duska J. Sidjanin, Brookfield, WI (US)

(73) Assignee: Cornell Research Foundation, Inc., Ithaca, NY (US)

( * ) Notice: Subject to any disclaimer, the term of this patent is extended or adjusted under 35 U.S.C. 154(b) by 290 days.

(21) Appl. No.: 11/157,743

(22) Filed: Jun. 21, 2005

(65) Prior Publication Data

US 2005/0282212 A1   Dec. 22, 2005

Related U.S. Application Data

(60) Provisional application No. 60/581,499, filed on Jun. 21, 2004.

(51) Int. Cl.
*C07H 21/04* (2006.01)
*C12Q 1/68* (2006.01)
(52) U.S. Cl. .................. 435/6; 435/91.1; 435/91.2; 536/23.1; 536/24.3
(58) Field of Classification Search ............... None
See application file for complete search history.

(56) References Cited

U.S. PATENT DOCUMENTS 5,804,388 A   9/1998   Aguirre et al.

FOREIGN PATENT DOCUMENTS

| WO | WO 9902731 | 1/1999 |
|---|---|---|
| WO | WO 0029615 | 5/2000 |

OTHER PUBLICATIONS

Acland, Gregory M. et al., "A Novel Retinal Degeneration Locus Identified by Linkage and Comparative Mapping of Canine Early Retinal Degeneration", GENOMICS, 199, pp. 134-142, vol. 59, Academic Press, San Diego, U.S.A.

Caase, C., et al., "A Gene Potentially Involved in Progressive Rod—Con Degeneration (PRCD)", Annual Meeting of the Association for Research in Vision and Opthalmology, May 2003, Abstract No. 2318, vol. 2003, Biosis Online Biosciences Information Service, Philadelphia, U.S.A.

Sargan David et al., Use of Flow-Sorted Canine Chromosomes in the Assignment of Canine Linkage, Radiation Hybrid, and Syntenic Groups to Chromosomes: Refinement and Verification of the Comparative Chromosome Map for Dog and Human, GENOMICS, Oct. 15, 2000, pp. 182-195, vol. 69, No. 2, Academic Press, San Diego, U.S.A.

Sidjanin, D.J. et al., "Radiation Hybrid Map, Physical Map, and Low-Pass Genomic Sequence of the Canine prcd Region on CFA9 and Comparative Mapping with the Syntenic Region on Human Chromosome 17", GENOMICS, 2003, 2003, pp. 138-148, vol. 81, Academic Press, San Diego, U.S.A.

*Primary Examiner*—Jeanine A. Goldberg
(74) *Attorney, Agent, or Firm*—Hodgson Russ LLP

(57) ABSTRACT

Tools and methods are provided for determining whether or not a dog is genetically normal, is a carrier of, or is affected with or predisposed to progressive rod-cone degeneration. The method is based on the detection of a transversion from G to A at position corresponding to nucleotide position 1298 of SEQ ID NO: 1.

14 Claims, 11 Drawing Sheets

```
   1 CGGCCAGGTG GCACCTCTGA CTCCCAGCCC AAACCTGATG CCAGTGTCCA
  51 CTTCTCCCTG TCGCTCCCTC GCGACCCCGC CCTTCTCAAG ACTTGGTGTC
 101 CCTCTGCAAG TGTGAGAAGA GGTCGGCTCA CCTCTTCCGC TTTGGCTTAT
 151 GTATTTTAAA AATCGTTTTT CAAAGTAGAG AGCCCAGGTG CAGCCCCAGC
 201 TCTGGCCCTC CCTGGGAGCC TGGGCAGGAG ACCCCTTGAC ACCGCTTCCA
 251 TCTCCTTGGA GGGAAGGAAA ATCTAGTGCA GACCYCTGGG GTTTTTGGAG
 301 AGGGCTGGAG GAAGCTGGAT GCTCAGACCC CTGTGTGCTC CACATGCTGC
 351 CTGGGCCACC TCACTGAACC CCTCTGACAG GACACCCGAT GCCTGTGCGG
 401 TGCCCTTCCA AGTGGCTGCT CAGAAGCTTT GCACTGGGAA AGCAAGTATT
 451 CGCTATTTCT ATTTAGTATT TCTATTTAGC TTTATCTCAT CTTTTACAAG
 501 TCTTATGTGT GTTTATTATG CAGGACTGTA TTCGCACAGA TGTGGAAGAT
 551 CTAATGTATG AGCAGATGCA TATACTTATT TCATGAGTGC ACACTTAAAT
 601 CCAGTCTTTT ATGGAAGGGG CTATGGAAAT CAGTAACATT TGGGGAGGAC
 651 TGTCCAGAGG GGAGAACACA ACTGCTCAGC CGCCCCTCCA CTCCCCGGCC
 701 TCCCTTGTCT TTCTGGCTTC ATTATCTAAT ATTCTTCCTC CCCTCCCCAT
 751 GGCTCTCCAT GACATCATTG TTCTGCCAAC ACTCAACTTC CAGTTGCTGG
 801 AACATGCTCT GTGCTTTTGT GTCAGCCGCC CCGGAAGAGT CTTCTGTTGG
 851 SGGGGAGGTA ACCTTCCTTG AACACCTGCA AATTCCAATG CCCCCAGCTC
 901 CTCTCCCAAG CATTCCCTGA CACATGCAAC TCCGAAAGTG CTCTGCGGGT
 951 GCCTCTCATC ACCCAAGTCG CTCTACTGTG GTCATTAATG TGACTTGCYA
1001 GCTCAAGTGT CTAGACTAGA AGCCCCTTGA GGGTTAGGCC CAGGTCCTAG
1051 TCACATCTGT ATCCAGAATG GACAGCTTGA TTTACCCTGC CACCGCAGGC
1101 GACAACTTGG GCCCAGTGAG GTTAATCAGT CTGCACAAGG TCGGGTTGGC
1151 TGACCCCACT AATCAGCTTG AGCCTCCTAA TCCAGTGGCA GCAGGAACCT
1201 CAGGATGGGC AGCAGTGGCT TGTGAGAGCC GGCAGGGCCA TTTTGGCCTT
1251 TCTCCTGCAG ACTCTGTCCG GGAGGGGATG GGGCAGCTGA GCCATGTRCA
1301 CCACCCTCTT CCTACTCAGC ACCTTGGCCA TGCTCTGGCG CCGCCGGTTC
1351 GCCAACCGGG TCCAACCgtg agaagctgat ggggccatgg gcagggatgg
1401 ggagagagga gaagctaggg ggtgaggggt ggtgcagggg ctgcctggac
1451 ctcctgggag gctggagggc gggaggatt tgcagggagg tccagagagg
1501 tttcccatca gagcacgcgg gggcggggc tcgcaggtgc tccgagactg
1551 gctggagtcc ccggtccccc agcccaacac ggccaggaga gggggttctg
1601 ggcccgggcg ctgcccacag ctcttccagc ctcttcctcc cgcccacagG
1651 GAGCCCAGCG GAGCAGACGG GGCAGTCGTG GGCAGCAGGT CGGAGAGAGA
1701 CCTCCAGTCC TCGGGCAGgt aaggcagagt ctgggctggg ggaggcaggg
1751 tgcgtcgagg aagcggctgc cctggccgcc ccgaccgtgc ctgggcaggt
1801 acatgagtgc acccgagccg gcgcgccggg gccctcgcc ccagccaccc
1851 ggtccccgtg tgcccggtgg gcagcctcgg tgtctgtgct ccccgcggc
1901 actgggcgcc csggcctgtc ctctgcaccg cagctgctct gctttgcccg
1951 agtgcggggt ggtccccgg gtcccatcgg aaggcgcggg gggaccggag
2001 aggatggggc aggagcagct ccgggcggcc ggctcgctgc ccttccccct
2051 ccccgcggcc cccgctccgc ctcagccgct cccctgcccc ggccgccggc
2101 gggattcgcc caccggcccc caataggagg cgcaggagcg gcatgacgtc
2151 atcggcaccg cctgccattg gctgggcagc tcctgcgggc aggtcgctgt
2201 ctccagcggc cgaaagttaa ctcttcccta ggccgaagcc atgtggctcc
2251 acaagggggg aagtttgggg aacttctgga ttcttccttc cctgggtgac
2301 cagtgtcctt tgatgttagg ggctcctatg cccaacaaac cacggaaaaa
```

Figure 1A

```
2351  tcaacatgca tttattaaga acataccgtt gtgcgtgttc ttttgtgccc
2401  ccggacccac ctrgtggggg agtcctgtgt gaagggacat tctctcctgc
2451  aaaaggtcta ctagccttct ctcaactcta gtgagacaaa gcacatgatg
2501  cccttgggct ccggggcctg tggctggagg gagtctcccc acagcgctca
2551  gatggctgag ccagtgagcg tgcctgcctg ctggggcacy ccaccggctc
2601  tcctccrggt gtgtaggacc tgcctgggtg cccctcagcc atgtggagac
2651  tggcgagcca tgagaaatga gaatgggaat ctgtctccgt atgcggcccc
2701  aaattcctcy tcggtgctgg gattcctcca agctctgaat rtcaggaggg
2751  cagccctggg catgtgccyg agacaggtat ttctgggcca cccttccttg
2801  acaatctagg ctagctgaga tggtcatgat actaccaag taggcctgct
2851  ggtgaaatgg gctgacaaag gtgaaatgat gagcactggg cctcacgcag
2901  agcaggccct tgaatgacta gtcctccctg ttgagtttgg gtctggaggc
2951  ggacagccag agtccacatc ctgactccct gcttcctgac cgagagcctc
3001  tgggaaagct atgtgatctt tctatttgta tataaactgg gattaataac
3051  agaatggtgt gggggtgttt gtgaggttca aattgagatc atcctaaagc
3101  acttggcacg aaacagctrt ttaataaatg ccggctagct attctcctgt
3151  tgttacctgg ctcttgatca gtgttctatt cttcccttga ggtctcttaa
3201  acgttaactc acttggaagt tgtaacagcc ccagagggtt ggcaagacaa
3251  gtgtttctat ctcttgttaa tggtggagga aactgaggga aggggaggcg
3301  tcagttttc actcgaggtc atccatccta tttgtggctg atggcaactg
3351  acttcaggta gtcggtctcc tctacatgaa atgggcctgg accctccctg
3401  tcaggagaaa aaagctgaat ctggaccatc tggcccagcc tcgtggggtc
3451  tagccagaag gaagcagttg cctgttaact cccagggacc cagttaactg
3501  gaaaaatcag cctaacatcc aacacctcct gcttcgggtg gctgttgtga
3551  agggctggtc tggggagcag taggcatgac atttctgctc tgcaattcca
3601  cagtcacaaa ttccagctga tttcctggct gctcctaccc ctcagtagtg
3651  gggtgcctcc ctaggcgtgg ggcaaaggga agaagtctgg aaagacggga
3701  aggacgtccc cttcaatcct ctgactccca tgcttttctg tttagAAAGG
3751  AAGAGCCTCT GAAGTAAGTC TTCACCCGGT CAGGCGGAGC TCGGCCCCAG
3801  GGAY TGGGAT CAGCTGGCAG AGGCAGgtag ggcagggctg caagccttgg
3851  aaggtagagg gctgggctgg ggacaaggca ggctctgcaa ggcctggcca
3901  tgagggagca gagctccatg gagggtacac agaaggcggg tggcctctca
3951  tcagctcctg cctcaagcct sctgtggtcc aggccatggc gcaaggcttt
4001  gttagtttta agggaagggc gtgtggtgaa gtggtggtca tgctggcact
4051  gtagtgccag aggacttcta agggagaggg tgtgctctgg aatatccatt
4101  ctgcaatgca agcccctgcc ttgggatggg aggaagtgcc aatctggttt
4151  tctatttcag TTCAAGTCCC GGCTGGCCTC TTACCCACAA AGCATGCTGT
4201  GGTGGAAGCA GCAGCAGCAG CAAGAAGAAA AATGGGAAAA AGCAGTCATC
4251  AAGAAGGTAG ACTCCTCCCT TGAGTCCCT GGACCTGCCT GGCCTCCCTT
4301  TGCCCCAGAC CCTGGTGGTG GGCTCCTGA AGCAAGGCCT GGCTGGGGCA
4351  GGCTGGAGGG CAAAGACGCT CATTGCCCTG GCTTGGGCTC CCTTCCTCTG
4401  AGATCCTGAG GATAGTCTGA GGCAGCCCA GAGAGGACT CAGGTTTCTT
4451  ATGGAAGGRC TTCTCATTCA TCCCTAATAT AATCCTTGCA ATGACCCAAG
4501  AAGACTGGGC GTGTTATTAT CCACACTTTT GGAAATGAGG AAACAGAGAG
4551  AGGTTAAGGA ATCTGTCCAG TGTCATCCAG CTAGTTAATC CTGCCCCCA
4601  CCCCCACCCA CCCCCCGCCC TCCCAGCCTC CTTTGGAGGC TGCAGAGCCC
```

Figure 1B

```
4651  ACACTCTTAC CCACCAGGGC ACAGGCCTCT CTGAAATCAC CTGGAAGTTT
4701  GCAGCTTGCA GCTGCTATGT GAGAGCAGGG GTTCCACGGG CCCGGCAGCC
4751  CCAAAGCCTG TGGTCCAAGG CTGTGTGGTA TCAGTTTGCC ATGGTGGCGC
4801  TCTAGTTTCC AGGGCACTTG CCTCTCCCCG GTCCCAGAG CTCACCCCGT
4851  CACCAGCCAC TCTGCTGCAG TTCTCAATAA GAAATGCCAG CTGGGATCTG
4901  TGACATGTCT GCCTGCGGCT GGAAGGAAGC ATCTCTCAAC CTGTCCTCTG
4951  AGCGTGTCTG CGTGCCTGTG TGCATGCGTG CGTGTGTTCC AAAGGGGCAG
5001  TCGCATGTGG GAAGGGAAGA AGCCTGACAC TTGTTCTTGT CAATCTGCTG
5051  ACTGCTCAGT ACCACGGCGG CTCTGCCATT TCTCCCTCAC AGTCCTGCTC
5101  GACCCAGAGC AGAGATCAAA GCAGATTTCC GCTTCTGCTC CCTGAGATCC
5151  AGGCGCAGAC CTGCAGGCAG CTGCTCCCCA CTGTCTGGAA GCCATTCATC
5201  ATGCAAAGCG CCTCCCCACC AAACCCCTGC CTGCACGTGC ATCRTCCCCC
5251  CACCATCACC ATCCAGCCCC CAGGGTGGGC AGGGAGGTCC CTGCCTAGCT
5301  GCACACCCCC CAGGCCATCA AGAGGCAGGA GATGGGGAGT TCTCTCGACA
5351  GCAGCCTGTC TGCCGCCCTG ACTCCACATC TGAGGGAAGG AAGGAAAGGG
5401  TGAGATGCCA CAGACAGAGG GGACCACGCT GAAGCCATGG GGGAGGGGCT
5451  GCTGATCTTG CCCTGGAAGC CTCTAGAAGT AGGGCAGGGT GGAGGCAGGG
5501  GAAGGGTCAA ACCAGGGGAA GGAGCTGTGC GCTGGAATGG CGACAGAGCC
5551  CCACCGCCCA CTCGACATGG GCCAGGAGTT CGTGACCACC TGTCTCAGCT
5601  CCTGTCAGCC TGTCTTTCTC CTGCGAGGTG TTGGCCTTCC TTGGTGACAG
5651  GGCTGTCGGG CTGAGGGCCA GGGGCACCGT TCCTGGGGCC CCCATCTKCG
5701  TCCCCGAGCC CACCTGTGTA TTCATCCTCT AATCTGTTTG CCATGCTCCT
5751  GTCACTTCAG CCTCGGCTCT GCTCTCTACC ATTTCCACGT TGCCTGCCTC
5801  CTTGCACTAG TCTGAGGAAT TGTCAGGCCA AGGTCACCTG GCTGGACAGG
5851  GGCTGGCCCA CGGCCCAGAC ACACCTCCAC GAGGCGACAC CCCTTCGCTG
5901  CACTGTTCTA GGGACCTGCT CAGGAGAGGG TGGCTCCTCT GGGCCTCGGT
5951  CCCAGAGGGA AGGAGAGAAG GGGAAGGGAA GGGCTGCTGG CGATGGGGGG
6001  ACTGTGTCGG CTGGCCTTGG CGGTTGCCCG GGCCCTGGCA GCTGGGGTGC
6051  CATGTGGGCT GGGCGGGAGG GGCCCTCTCC CCCAGGGAGC AGGCTGGCTT
6101  CGGTGGGAGC AGATTGTGTT TACACCTTCC CCACACACCC AGCCCACGCT
6151  CGCCTCTTAT TCCCCGGGAC TCTCCCACCC CTGGGCTCTC TCTGCACCAC
6201  GGGCACGTTT GCAGCTCCTC TCCTGCTGCA GGAAGTTGCC GCCCTCAGCA
6251  GAGMGCTCCT CTACAGAAGG CTGCCAGGGC CCAGGCGCTC CCTCCTCGGC
6301  CCACTATCTC CCGTCGTGGG GGGGACCCA GTGTCCCCAA GAGGCTGAAT
6351  CCACCCACCC CCCATTTCCT TGGAAAACAG CTGCTGCTTG GGAATGGGGG
6401  CAGGAAGGAA AGCCCGGGGG GCTTGGCAGA CTTGACCATA ATAGGAGGGA
6451  AGGGATTAAG GGCAACCAGA GAGAGGGC CGAGAGAGCC GGGGCGCCTC
6501  TGGCCTCAGG GTGCATGAGA TAATGTAGAA TTTAAGCTCG GGGAGTCCAG
6551  CTCCAAGCTC TGGATTTGAA TCTTGACTCC ACCATCACTT TCCAGTTCTG
6601  TGGCCTCGGG TGGGTTACTG AATGTAAACC TGTCTCAGAG TTGTAAGGGT
6651  TAAATTAGAT AATGGGTATA AAGTGCTTCG CGCACTTAGT AAGCACGCAG
6701  TATATCTGAG CCCAGGGTGG GGGGACAGTG TTTGTGAGCT GTCAGCCACT
6751  GAACAACTGG TCACTTTGCA ACAACCGTAG GTTCAGAACA GCTAGTCCTT
6801  TACCTCCTCA CCCCATGGCC CTTCCTGCCC TGTCTTTCCA CATACACAAC
6851  AGCAGGGTGA TGGGCAGTTC TGGAACAAAC CAGAGCCCAG CACAGGGGCA
6901  CCTGGTAGGA CCCAGCACCC GGGAAGGCTG GACGATGGAG CACCACGGTT
6951  GCYTCTGGGT GCCTGGAACC CTGTCCCCAC CTCCAGTGGG AGTCCTGACC
```

Figure 1C

```
7001  TGGACATCTT  CCCTCCAACT  GGCTCTGCGW  CCCCAAATGA  ATCTCAGCTC
7051  CTAGAGAAGA  CAGGAGGCCA  TGGCCCTGGT  GCCTTTATGG  TCCTCTGTCT
7101  GAATGCTAAT  CTCTTTACTG  GCTGGAGCCT  GAGTGACAGG  GAAAAGGCGG
7151  TTCTGAGCTG  CAGGGTGGCC  GAGGGCGGCA  GGMGGGAGCA  GGGAGGTGCT
7201  GTTGTCTGCT  ACTTCTGTGG  CTGCTGCCAG  TCTCTCCTRG  AGATGGGAAC
7251  ATGACCAGAG  AGCTAATGAG  GTGGCGGGGG  TGGGGTGGG   GGAGAAAGGG
7301  AGGCAGACGG  AGCAGCTGCA  GCAGCTGCCA  CTGCCCTGTG  TCACCCCAGG
7351  GTGCAAATGC  CACCACGGGG  AGCACCCCGC  CCATCCCGAA  CTGTGTGGCT
7401  GTGCAGATGC  GGGCAGGATG  GTCCTGGGCA  CAGGCCTTGG  TCCAAGACCA
7451  GGCAGGCGTG  GTACTTGATC  TGAGGTGGGC  ATCATGGCAC  AGGAGCTGGT
7501  CCCAGGGGTG  CCCGGGGACC  TTTATAGAAC  CTCAGTCGGG  AAGAAGCCCA
7551  AGACCTTGAG  CCAGAGGGAA  GTAATGCTTC  TTTGTGAGCC  TCAAAAGGAG
7601  GGAAATGGCC  AAGGTTTACA  GTAATATAAT  GACACTAATA  TTATTATTAA
7651  TAATGGCTAA  TGTGTCTCAA  ACGCTTCTTA  CGTGCTAGGC  GCTGTGCCAA
7701  GTGCTTTATT  TATATGCATT  GTCTCATTTA  TGGGGCAGGA  ACTGTTGTCA
7751  GTCTCATTTA  CCCAATAAGG  AAAGTGCTTG  CTCAAGGTCA  CCCACAGTGA
7801  GTAGTGAAGC  CAGGACGTGT  TCCCCGGCAA  GGTGATGTAA  AAGCCTGTGA
7851  AGGTRTTGGG  CCTCGAGGAC  ATCCTGGGAG  TGTGACCTGT  CCACCAGGGC
7901  ACAGGGCATG  AGAGCTGGCA  ACCCTCCCTG  GTGATACTGC  CGCTGCTCAG
7951  TCTGCAGAAA  CTCATCATTC  CAGGCTGGAC  CAGACTCTGG  GCCCCGAGGG
8001  CAGTGACCAG  AGCCACCTTT  CCAGGATCTG  TCATGCTCCT  CAGGGAGGAA
8051  GCAGTGGCCA  CTGGCAGGGA  TGACAGATAT  CAAGGTTGTC  ACTCATTGCT
8101  GCTGTTGCTC  TGCTGTTTCC  TCCAACCAGG  GGCAGAGCCC  TGGGGGTAAG
8151  GGAGGGTGGC  AGCCAGCAGC  CCAGCCAGAG  AAGGAGGAGC  CAGAGGAGGA
8201  AGGCTTTGTT  GTTTGTTTTT  ACAGGGGGAY  GGTGCAGGGC  TTTAAGGAGG
8251  TGGCTTCAAG  ACCTGCTGAC  TTTAGCCATA  AACTGGTACC  TAAGGGTGCT
8301  GGACCCTCTC  TGTGGGATAC  ATATGCCCCC  TAGTGGGGAT  TAAGCCTGGA
8351  GGGTGGCTGA  GAAAATTAAA  GCAAACAAA   ACAAAAAAG   ATTTACTGAT
8401  AGGCTATATG  ACCTCCGAAC  CTGGATAGGA  AGGGCCAGGG  CTGGCCCCCT
8451  GTGTCCCCGA  GATTGCACAA  GCACGCACAG  GTTTAAGACA  ATTTGCAGAA
8501  CCCAGGTGAA  CGAAGCATTG  AAAGAAATTA  TTTAATTTAT  TCCTTGGTCA
8551  TTTATTTAAG  AAGCATGTAT  CGGGAGCCTG  TGATGTACAC  ACCCTGTGGT
8601  AGGTGTTGGA  GTCAGACAGC  AATCAAAGGG  ACGGCGCCCG  ATGTGCCAAT
8651  GAGGACGACA  GAAAGATCCT  GGCCGAGGAG  GCCAGTTGTG  CAAGCTCAGC
8701  CGCTGCCTGC  CACGACTTTT  ACTTCTCTGG  ACCTCAGTCT  CCCCATGTAA
8751  TAGGCAGTGT  TGAACCTAAG  TGGGCTGGTG  CAGAGGATGG  GAAGGACCAC
8801  TGACTACCCT  GGTAAAATGA  AGGGGATGGA  CTTCTTGACC  TCGGGGGGG
8851  CCCTTCCAGA  TTCAAGACAG  GCTACAGTGG  ACAGTGTTTG  GAGGTGCTGA
8901  CAACGGTGAC  TCGCCCACTC  AGCAAGCGTG  TATGGAGCTC  CTGTATGCCA
8951  GGCATTGTGG  GTGGCAGAAA  TGAAGCRCCC  AGAAAACTGG  ACAAAACTGA
9001  AGAAGCAACA  GACACTTGAC  TACAAGGAAC  ATCCAAGATG  GTGATCCCGT
9051  GACCACCTCA  GCATCTACCT  CCCACAGGTC  CCTGCCTGAG  CACAGGGAGG
9101  GGAAACCCAG  AGGACTGCAG  TGGTCTTGTT  CAGCTGAGGA  GACAAGATCA
9151  GAGCTCAGAA  CAGTGTGCTG  TTCCTAAAGA  TATACACACA  CATCAATGGC
9201  ATCTCCAAAA  CAGACACAAC  GAAGATGATC  CAATGGAGAA  AGAAAAGCCC
9251  TTTTGAGGAA  ACACAAAAAG  TGCTAACCAT  AAAAGAAAAA  AACAGATAAA
9301  TTGGACTTGA  TCAAAATTCT  TGGAAAGACT  GGAAGAGAAT  ACTAGCCAAG
```

Figure 1D

```
9351   CAAAAATCCG AACAAGGGCC TGTATCCAAA ATATATAAAG AACTTTTACA
9401   ACTCAATAAG AAGACGACAG CCCAACGAAA AAGTGGGGA  GGGTTTTAAT
9451   AGACACTTCG CAAGAAACTA GACATATGGC CAATAAACAC ATAAAAAGAT
9501   ACACAACATC CTAAGCCATC AAGGAAATGC AAATTAAAAC CACAATGAGA
9551   TACTACTGCA CACTCACCAG AATGGATAAA AGATGGACCA TAATAGACGT
9601   GGGTGAAGGT GTGGAGCAAC TTGTAACCCT GTCATACGTT GCTGGGAAAC
9651   CTGTTTGGCA GTTTCTTAGG ATGTAATCCA AGAGGAGTGA ACATGTAGGT
9701   CCACACAAAG ATTTGTACAG AGATGTTCAC AGCAGTGTTA TTATCAATAA
9751   TTAGTATCCA AACTGGAAAC AACGCAGATA GCCATCAAGA GGTAAATGGA
9801   TAAAAAAAAA AAAAAAAAAA AGGAGGCGGT GTATTCATAC AATGGAATAC
9851   GATTCAGCAA TAAAAAGGCA TTGAGCTACT ATGTGAGCCA TAACACAGGG
9901   CAATGAGAGA AGCCAGATGC TAAAGAGCAC CTACAGTATG AATCCATTTA
9951   TAGGAGATTC TAGAACAGGC AATAACTAAT CGGGAGTGGC AGAAAGCAGA
10001  TCAGTGGTTG CCCGGGGCCA GGGCTGGATA TGGACACTGT GAAATAGCAG
10051  GTTGGTACCC TCCAGGGGGA TGGAGATGTT CTAAATTGAG ACTGGGGTTG
10101  TGGTTTTATG GGTGTATCAC TGGCTGGACT ATTTTAAATG GATGCACTTT
10151  GTTATATGTA AATTATACCT CAATAAAGAT GACTTAAAGA GTTAAAAAAA
10201  AAAAAAAAAA AAAGAACCAC GAGAATGAAR ACCTGATCCT TGTCTTGCTT
10251  ACAGTCTAGT GAAAACGMCA GATGTGAAAA CAAACAACCA TAAGGCGGTG
10301  AGTAGCCTAA GAAGCATGCT CAAATAACAA GAGTTCTGTT TATGAAGGGC
10351  TCCCTCGCGC CAGACCCACA GAGGTGGCTT GGCGTCACTG TTCTAGAAGT
10401  CCAGATAAGA AAAGAGGCTG AGATGGAGGG GAAGTTGTTC ACGCAGGATT
10451  ACTCAGCTAG AATCAGCAGG CCTGGGACTG GCTCCAAGG  CTGCCTGGGT
10501  TCAGAGCAGG TGCCACAGCA GCCTGTGGCA GGACACCGAG CAGAGAGCTC
10551  GGGACTGTTG CAGCTTCTCA GGTGAGACTT TGCGGAGGAG GTATTGACAC
10601  AGGAGTTGGA ATTTGCTCAG CAGAGTAGAG GATGCGGGGA AGGAAATTTC
10651  AAAGCAAAGG GAACAAACAA TATGAGCAAA GGCTGGGCAA CACTTGTGAG
10701  AAGGCAGGGT TCCTGGGAAT GGAGAGACGT GTCCCGAAAA GAGCAGAAGA
10751  GGTCAACAGG ATATTACATG TTCTTCGCAT TCACTTATTT TTTTAAGAAC
10801  CTATTAAGCA ATAATTTTA  CGAGAGGCAA CAGCTCTGCA GGGCAGGCAA
10851  GTGAWGTATG TGCTCTTGGC AAACGCAGGG AAGAACCCAC CGTGATGCCA
10901  AGGTTGCCTC TTTAGGGAAA GGGGTTCTCC CTGTGACATT TCTCCTCCTC
10951  CAGGAGGTTA AGGCTGTGTT CCAGGATCCC AGGTTTCTGC TGAACACCCT
11001  TTGTGGCACT CTTTCACGGT CCTGAGAAAT CCCAGGAGGA AAAAAAAAA
11051  AACAAAAACC CGCCTGTGCT TTTATGCTGG GCTTTCTGGC TGGAGGAAGT
11101  CAAGTCACTG GAGCGAAGCA AAATGTGTCA CACTGTCATG GTGCGTTCTT
11151  CTGGAAACTC AGCACAGCAG TGAGGTTTGG AGGCTTTGAG GCTGGACTGG
11201  CTGAGGTCAG ATCTCAGCGC TCTTTCACAC TGATTACTTT CCCCTTTCTG
11251  CACTTTGGCT TCTTTAGAAG ATTGCAAAAG AGGGGTGATC ATAAGAGGGC
11301  AGATGTGAGA ATGAAGGGAC AGTACGTGCA ATGTGCTCAG TCAGACTCAT
11351  CGAGTCTGAG ACGTTAATTT AGCCTGTATA GCCTTTTGTA TGACAGTCAG
11401  TCCTCCATAA ATCAGTTTTT TAAAAGAAG  GTGCTTAGAG CAGAGCCTGG
11451  CCCAGAGCAA ACATTTAATA GACAGTAGCT TTTGTGTTTT CAAAAGGTG
11501  ACATGCACAT GTCATCCCTT TTATTTTGCT GTGACCCGTT CTTTCAGAGA
11551  ATTATAATGA AGCGGGATTT GGGACATGTT GATCATATCA TTTAGGATGA
11601  TTGTGACTCT TAACAGAACA CCCAACTTAG GGTGGCTCAA ACAGGAAGGA
```

Figure 1E

| | | | | | |
|---|---|---|---|---|---|
| 11651 | GATTTCTAAA | TCTCACATTC | TGGGGCGCCT | GGGTGGCACA | GTTGGTTAAA |
| 11701 | CATTCGACTC | TTGGTTTTGG | CTCAGGTCAT | GATCTCAGGG | TTGTGAGATG |
| 11751 | GGGCCCTGTG | TTGGAGTCTG | CGCTCAGCTC | ACAATTCTCT | CTCTCCTCCA |
| 11801 | CTTCTGCCCC | TCCTGCCCTC | TCTAAAATAA ACATTGAGG | | GTTTTTTTAA |
| 11851 | AAAGATTTTA | TTTAGTTAGT | TGAGAGAGAG | ACAGACAGAG | ACAGAGAGAC |
| 11901 | AGAGAGTGAG | CATGTGTGAG | CACAGGTGGG | GAAGGGCAGA | GGGAGCAGCA |
| 11951 | GAATCCCTGC | TGAGCAGGAA | GCCCAACACA | GGGCTTGATC | CCAGGACCAA |
| 12001 | GATCAAGACC | CGAGCCAAAG | GCAGATGCTC | ATCCAACTGA | GCCAGCCAGG |
| 12051 | CAACCCTAAA ATAAATGTCT | | TTTTTAAAA | AATCATCCTG | TGTTTCACTG |
| 12101 | AAACTAACAT | GCCATTGCTT | GTGAGATGCC | CCTTGCATTC | AGAAATATTA |
| 12151 | AAATATAAAA | ATGTGTGTCT | TTGARTTGAA | ACAAAAGGTC | TGAAGGTAGG |
| 12201 | GGGCTCTAGG | ACTGGTAATT | TGGCAGTTCA | CCATGAGGAC | TCTTTGTCCT |
| 12251 | TTGTTTCCAC | TCTGCCATCG | TCAGACCTTA | GGCTCTGGCT | TTGAGGCAAG |
| 12301 | CCTCATGGAT | GCAAGATGGC | TGCCAGGGCC | TCAAGCATCA | AGTCTTCAGA |
| 12351 | GCCTCCCAAA | GCCAGAAGAG | AGGCTGCTGT | TTTTAAAAAC | AAGAAAAACT |
| 12401 | TTCCCAAACT | TTGCTTAATT | GCATCACAAA | CCCTTTTCTG | AATTCCTGGC |
| 12451 | AGAAGGAATA | GATTTATCAT | AAGGGTCTGG | TGCCGACTCT | TCAAGATTCG |
| 12501 | CCCTTAGGGC | CGGGGAGGAG | CTTGCCTCCA | CTGAAGCACC | GAGCTCCAGT |
| 12551 | TCTGTTGTGA | GATGGAGGAA | GAACAGCTGT | GAGCTGGCAA | TGAGCAGCGC |
| 12601 | TGCCATACAG | ATRAACCGCC | TGTGAATCAC | CGGTCAACTG | TGCCCGACAG |
| 12651 | AAGCAGCTGA | CTGCTTGGGA | TATTCCTACC | CACCTTCCTG | TTCCTATCAA |
| 12701 | CAATGGTAGA | GCTTCCTCTC | CAGGTTAAGA | AATTAACCTC | CATATTCCAA |
| 12751 | AGACTTGGTT | TCCTATTAAT | GTGGCTTTCG | GGTACCGTAT | CCAAAATCCT |
| 12801 | ATCCGGATGG | AACCCAGTGA | GTTAGCCACC | TGAGCACAGC | AGGCCAATGG |
| 12851 | ACTAGATTTC | ACCTCCGTGC | TCAGAGCCAA | GGCCCCTGA | CCGCACCGAG |
| 12901 | GACTGTGGCC | TTGCTCAGCC | TGGGATCTAC | TTCTGTCACT | GACCACTAGA |
| 12951 | TTGGGGGACT | CCGTGTCAGT | GAATACAGAT | CCATGCTAGC | CTAGGATGAC |
| 13001 | GGCTACGTAA | CAATTCCACT | GCAATAAAA ACTCAAGTGT | | CCCAGACCTC |
| 13051 | GGGGCGCCTG | GCTGGCTTAG | GGAGGACTGA | CTCTTAATCT | CAGAGTCTTG |
| 13101 | AGTTCAAGCC | CTGTGTTGGG | TGTGGAGCCT | ACTTAAAAAA | AAAAAGAAGA |
| 13151 | AGAAGAAGAA | GGAGAAGGAG | AAGGAGAAGG | AGAAGGAGAA | GGAGAAGGAG |
| 13201 | AAGGAGAAGA | AGAAGAAGAA | GAAGAAGAAG | AAGAAGAAGA | AGAAGAAGAA |
| 13251 | GAAAGAAGAA | GAAGAAGAAG | AAGAAGAATT | AGAAATCACA | ACATTGATGC |
| 13301 | TTTGATCTCC | ACAGCTCTGA | ACTCCGCCT | GCTCCTTCAG | AAATCTGATG |
| 13351 | CGTTCTCTGT | TGTCTTTCCA | CTGATTTTTT | TCTTTTTTTT | TTAAGATTTT |
| 13401 | ATTTATTTGA | CACACAGAGA | GATCAGCAGG | GGGAGCATCA | GAGGGAGAGG |
| 13451 | GAGCAGCAGG | CTCCCGCTG | AGCAGGAAGT | CCAACATGGG | GCTCAATCCC |
| 13501 | AGGACCCTGG | GATCATGACC | TCAGCCAAAG | GCAGATGTTT | AACCCACTGA |
| 13551 | GCCACCCAGG | TGGCCCTGAT | TTTTTTTTA | AGATTATTTA | TTTATTTTAG |
| 13601 | GGATCCCTGG | GTGGCGCAGC | GGTTACCGC | CTGCCTTTGG | CCCAGGGCGC |
| 13651 | AATCCTGGAG | ACCTGGGATC | GAGTGCCACA | TCGGGCTCCC | GGTGCATGGG |
| 13701 | GCCTGCTTCT | CCCTCTGCCT | ATGTTTCTGC | CTCTCTCTCT | CTCTCTGTGT |
| 13751 | GACTACAATA | AATTAAAAAA | TATTTTTTAA | TATTATTTAT | TTATTTTAAA |
| 13801 | ATATTTTATT | TATTTATTCA | TGAGAGACAC | AGAGAGAGAG | GCAGAGATAC |
| 13851 | AGGCAGAGGG | AGAAGTAGGC | TCCCACAGGA | CTTGATCCCA | GGACCCCAGG |
| 13901 | ATCACGACCT | GAATCCAAGG | CAGATGCTCA | ACCACTGAGC | CACCCAGGTG |

Figure 1F

```
13951  TCCCATTAAA GATTATTTAT TTGACAGAGA GAGAGAGAGC AGGAGCAGAG
14001  GGGCACAGGG AGAAGAAGAC TTCCTGCTGA TCGAGGAGCC CGACATGGGG
14051  CTTGAACCTA GAACCCTAAG ATCATGACCC AAGTTGAAGG CAGATGCTTA
14101  ACCAATGGAG CCACCAGGTG CCCCATCCTC CCCTATTTCT GGACTGCCCA
14151  GGCAGTGTGC CCTCTGCCTG CCACTCTTCC TGCTTGTGTG CTCTATTTTT
14201  CAAATAAATA AATTAATTAA AAAATAATAA TCTTGAGGCA CCTGGGTGGC
14251  TCAGTGGTTG AACATCTGTC TTTGGCTCAG GGCGTGATCC TGGGGTCCTG
14301  GGATCGAGTC CCACATTGGG CTCCCTGGAT GGAGACTGCT TCTCTCTCTG
14351  CCTGTGTCTC TGCCTCTCTC TCTCTGTGTG TGTGTGTCTC TCATGAATAA
14401  ATAAATAAAA GGGATCCCTG GGTGGCACAG TGGTTTAGCG CCTGCCTTTG
14451  GCCCAGGGCG CGATCCTGGA GACCTGGGAT CGAATCCCAC GTCGGGCTCC
14501  CGGTGCATGG AGCCTGCTTC TCCCTCTGCC TATGTCTGGG ATCCCTGGGT
14551  GGCACAGCGG TTTGGTGCCT GCCTTTGGGC CAGGGCGTGA TCCTGGAGAC
14601  CCGGGATCGA ATCCCACATC GGGCTCCCGG TGCATGGAGC CTGCTTCTCC
14651  TTCTGCCTGT GTCTCTGCCT CTCTCTCT CTGTGTGACT ATCATGAATA
14701  AATAAATAAA ATCTTAAAAA AAAATAAAT AAATAAAATC TTTTTATTAG
14751  ATTTTATTTA AATCTTTTTA TTAGATTTTA ATCTCACTGC GTTTTGCTCC
14801  GGCCTCTCGG CGCCTGCCCA GCCACCCGAG ACATGCCACC TGCGGTGAAC
14851  CTGCTGCTCT TCTACTAGGT GTCCTGTCAG GTGTGAAAGC TCCACTGTAG
14901  ACCGTGGCAT TGTGGCTCCT CTCAAGCCCA GAAGAATGCT CCATGCTCCT
14951  CACACGCACT AGCTGGCAAC CGGTCTGGGA CTCAAGACAG CCCTGCTAGA
15001  GCCCAGAGCC CCCCAGTCTT GCAGCCATCA GCYCCTGCAG CCTCTCCTCC
15051  TCACTCTGCT TGCCATAAAG TGGCTCAAAA CCACGGAACA GGTGCCCATC
15101  ATTCCCCTGA GTAATTTCAT CCCAACCACC CCTGCAAACA CACAAAACCC
15151  TTCTTTGCTC CTCTCCCCCA TGCCCAAAAG CCCTATAGTA AGACTGATGT
15201  ATAGATATAC GAAGTTCAGT ACATCTTAGT GGTGAGAGTA TGGACTCTGC
15251  AGGCTGGCCT CAAACCTTGA CCCCAGCAAT CACTAGTTGT GTGAATTTGG
15301  GAAAGTCACC TCATCTCTCA CTCACCTCAC CTCATCTGCG AAATGCRGGT
15351  AGTGATAGWG CCCTTCAGAG GGCAGCGGTG CACATTAAAC AAATTGGTGT
15401  GCGTTCAGTA CTCCAGGAGT GGACGGCGCA TGGTAAGTGC TACCYGGTAT
15451  CCACTCTCGC TGTTATTCGG CCTGCAGCGG GTCCCTTGCC TCCATCCAAG
15501  CAGCTCTGGG GAACTTCCAC ATTCAAAACT CCCTCTCCGA GTCTGAAAAT
15551  GAAAGGAACT TAGTTTTCAG GGAGAGAGCC CATTCCTCCT TTCCCTATTC
15601  TACAAAACTG TATTCAAGGG CAAGACAGAA ATGCAAGGGC CAGTTTCATA
15651  AGACAGATGT TACTGCCAAG TGAGTCAATG ATTATCTGTT GTGTACGTGG
15701  GCAGAGGCAG AGGAATAACA ACCAGACTCT GGGAGGCAAT TAAAAAGAAA
15751  AAAAAAAAAA GTAAAAGAGT GTCTCATGGA GCGCCTGGGT GGCTCAGTCC
15801  GTTAAGCCTT GGACTTTTGG TTTCCCCTCA GGTCATGATC TCAGGGTCGT
15851  GGGACCCAGC CCTGGGGCGG GCTCTGTGAT CAGTGGGGAG CCTGCTTGAG
15901  ATTCCCTCCT TCTGCTGTGC ACACTCTCTC TCTAAAATAA ATACGTCTTT
15951  AGAAGAGCAA GCGAGCGAGA GATGCTTCCC GCCTAGAAGA GCTTACAATC
16001  AAATCAAGGG AGGCAAACAT AAACAAGTGT GGCAACTTGA TAATAAGCAC
16051  CTGCGACCTA TGGCCATACA CAGAATAACA TAACCCAGAC TAAATGCCAC
16101  TGCATAGTCA CTAGCGGGTT GATGACAACG GGGGAGGCT AATGCTGAAA
16151  AGGCCTTTCT GTCTTATAAG TTTAAACTAA TTTCTGGGGG CACCTGGGTG
16201  GCTCTGGTTG AGCATCTGCC TTTGGGTCGT CGTCCCAGGG TCCTGAGATC
```

Figure 1G

```
16251  GAGTCCCTCA TCCGGCTCCC AGCCCCGTAG GAGCCTGCTT CTCCCTCTGC
16301  CTCTTCCTCT CTGTCTCTCA TGAATAAATA AATAAAAATT TTAAGGGATG
16351  CCCGGGTGGC TCAGCGGTTT AGCGCCTGCC TTTGGCCCAG GGTGTGATCC
16401  TGGGGTCCCG AGATCGAGTC CCACATCGAG TCCCACATCG AGTTCCGGGA
16451  TCGAGTCCCT GCAGGGAACC TGCTTCTCCC TCTCCCTGTG TGTGTGTCTC
16501  TCTCTCTTTC TGTATCTCTC ATGAATAAAT AAAGAAAATC TTTAAAAATA
16551  AATAAATAAA AACAGTATTT AAAAAAATGA ACTAATTTCC AAGTAGGTGT
16601  AAATTCTGGC TCGGACTAGT GAATGGCTCT GGCTCTGCTG CATCACCCAC
16651  CGCCAGGGCT CTGGGCCGCT CCGAGCCCCG CTCGCCGGCG CCCCCTGCCG
16701  CCCGGGCCTC CCGCCTTCAC CCCAACCCGC AGGGCGGCGG AGCCCTAGGC
16751  CCAATCGGCC CCGGGAACCT GCCGCCTCTT CTCTAGCGCA ACCCAGCACC
16801  CAGATGACCC CTTTTCCGCC CCAGGTGCAG TCCGGCCGGG CCCTGGTGTC
16851  CTCACCCGTT CCCCTAGGGA GACCCCTCTC GAACCTTCTG CGCCACCCTA
16901  CTCTACGCCA GGGAAAATCT GTGCACTCAG TAGATAAATG CTTGTAACTG
16951  AAGCAACCGT CTCCGTGGCT CCAGAATCGC GCTGAGGATG CTGCTGCCGC
17001  ACCCCCACCT CCCCCGGCTC CGGCGGAGGT TGTTTGGACT ACACTTCCCA
17051  TGAGGCCCCT CTCAACATCG CGATAACTCT CGCGAGACCG CTGGGAAGAG
17101  TTGTGCGCAG GCGCAGCCCC GCCTTCTTGT CGAGGCAGGC CGCGTGGCCG
17151  GCAGTCATGG CGGCTCCTTG CTGGCCCGAC CGGGACAGGG AGTCTGGAGY
17201  CTCTGGCTGT GGTAAGGTTG TCGAGGCGGG CAGACGGGAT CGTCCTTGGC
17251  CCGGCGCTAG TTCGCTCGGC CTCCCTTTCC TCGGGGGCGG GATGATGACG
17301  GTAAAGCCGG TCTTCCTCGT AGGGTGGTTG GGTTAGTTGA GATGCTGGAT
17351  CGGAAAACGC TTTCTGAGCG GCGCGAGTGT TGACGATCGA AGGGAGAGAG
17401  CTCAGGCCCC CCTTGGAGTC AGAGGGCCCC TCCTGGGGGG GGGGGTCCTC
17451  CAGCCTGTGC AGCCCGTGT GTGCCCTGCG GGTCTCCCGG GCCCGCCCAC
17501  GGGAGGCTGC CGGTGGTAGT TCTTAATCCA CATCAAGTGT TAACGTGAGG
17551  GTCCTGGAGT GCCCCGAGGT CGGCCCTGGT CAGTGGTTCG TATTCAGTCC
17601  TACAGATAGT AGTAAAGGGG CTTGTAGATT TTGGAAAGCC ATAATGCTCT
17651  GCGCCCTACC TTCCATGTTC ATTTTTTTC CCCTCTCTCT TCCCGTACAG
17701  GGTTTTCTTT GCGTCGCAGA CCTGCAGGTT GAAGCTTAAA AGTAGCAAT
17751  GGGGAGCCCT GTGAAATGGG TAAGGATGGG TGCTGGCAGG GCCCGGGTGG
17801  TGACCAGAAG TGAGAAAGTC GAGATGGTGG GCAGGCCTGC CACACCCGGC
17851  CGCCGCACGC TTTACTTTAC TAATTTTATT TTTTTTAAA GRTTTAATTA
17901  ATTAATTAAT TAATGATAGG CAGAGACACA GGCAGAGGGA GAAGCAGGCT
17951  CCGTGCCGGG AGCCCGACGC GGGACTCCAG GATCGCGCCC TGGGCCAAAG
18001  GCAGGCGCCA AACCGCTGAG CCACCCAGGG ATCCCACTTT ACCGATTTTA
18051  AGTTCGGTTC TTAGGAACAC GTGGACGCAC GCATCCGGTT AGGGTGAGAA
18101  GAAAACGGAC CCGGGTCCTG GAAGCGAGCA GGGCCTTGCC AGTGTGACTC
18151  GGCGCCGCTA GGTGTCACTG TTTGGATTCA AACCGGTTGC CGCGCACGAG
18201  GTTGGCGGGG AGGCTTAGGA AATGGGCTTC GGTGGGGTTT GGAAGTATTT
18251  GTGGATGATT TAAAGTTATC TTTGTCTTAA AGGGCTCTTT TGTGAAGAGT
18301  TTTGATGCGT TGAGGCTCAG CTTTTTTTTT TTTTTTTTT TAAGGTTTGT
18351  ATTCATTTTT TCACAGAGAG GCAGAGGGAG GAGAAGCTTG CTGCCTGCAG
18401  AGAGCAGGAT GCGAGACTCG ATCCTGGAT TCGGGATCA CGCCCAGAGC
18451  CAAAGGCAGA CACGCAACTA CTGAGCCACC CAGGCGTCCC GAGGCCCCAG
18501  CTTCTTAAAT AACCAATCTT GAGAATAACA TCTTGACCTC ATTTCTCTTA
18551  GAATATACTT TGTTACATTT CCCTTAGAGA TTAAAGGTGT TG
```

Figure 1H

```
  1  AGTGGCAGCA GGAACCTCAG GATGGGCAGC AGTGGCTTGT GAGAGCCGGC
 51  AGGGCCATTT TGGCCTTTCT CCTGCAGACT CTGTCCGGGA GGGGATGGGG
101  CAGCTGAGCC ATGT[R]CACCA CCCTCTTCCT ACTCAGCACC TTGGCCATGC
151  TCTGGCGCCG CCGGTTCGCC AACCGGGTCC AACCGGAGCC CAGCGGAGCA
201  GACGGGGCAG TCGTGGGCAG CAGGTCGGAG AGAGACCTCC AGTCCTCGGG
251  CAGAAAGGAA GAGCCTCTGA AGTAAGTCTT CACCCGGTCA GGCGGAGCTC
301  GGCCCAGGG AYTGGGATCA GCTGGCAGAG GCAGTTCAAG TCCCGGCTGG
351  CCTCTTACCC ACAAAGCATG CTGTGGTGGA AGCAGCAGCA GCAGCAAGAA
401  GAAAAATGGG AAAAAGCAGT CATCAAGAAG GTAGACTCCT CCCTTTGAGT
451  CCCTGGACCT GCCTGGCCTC CCTTTGCCCC AGACCCTGGT GGTGGGGCTC
501  CTGAAGCAAG GCCTGGCTGG GGCAGGCTGG AGGGCAAAGA CGCTCATTGC
551  CCTGGCTTGG GCTCCCTTCC TCTGAGATCC TGAGGATAGT CTGAGGCAGG
601  CCCAGAGAGG GACTCAGGTT TCTTATGGAA GGRCTTCTCA TTCATCCCTA
651  ATATAATCCT TGCAATGACC CAAAAAAAAA AAAAAAAAA AAAAA
```

Figure 2

IDENTIFICATION OF THE GENE AND MUTATION RESPONSIBLE FOR PROGRESSIVE ROD-CONE DEGENERATION IN DOG AND A METHOD FOR TESTING SAME

This application claims priority to U.S. provisional application No. 60/581,499, filed on Jun. 21, 2004, the disclosure of which is incorporated herein by reference.

This work was supported by Grant No. EY006855 from the National Institutes of Health (NIH). The Government has certain rights in the invention.

FIELD OF THE INVENTION

The present invention relates generally to a class of genetic diseases, observed in canines, termed progressive rod-cone degeneration ("prcd"). More particularly, the invention relates to a gene and a single nucleotide mutation in the gene associated with progressive rod-cone degeneration in dogs.

BACKGROUND OF THE INVENTION

Progressive Retinal Atrophy (PRA) is a heterogeneous class of retinal disorders that share a broadly similar clinical disease phenotype, and affect the dog (*Canis familiaris*) (Aguirre, 1976). The clinical features include: initial night blindness followed by reduction in photopic vision leading to complete blindness; reduction in retinal vessels, and retinal thinning; abnormalities in an electroretinogram ("ERG"); and the development of cataracts. Diseases of this group are typically inherited by means of an autosomal recessive gene defect although dominant and X-linked forms of PRA also are recognized (Kijas et al., 2002; Zhang et al., 2002). PRA may be classified into developmental and degenerative diseases. The developmental class comprises several genetically distinct diseases expressed cytologically in the immediate postnatal period when visual cells in the canine retina begin to differentiate (Acland et al. 1989). In contrast, the degenerative class represents defects in which photoreceptor cells degenerate after having differentiated normally—this class includes the specific disease termed progressive rod-cone degeneration (prcd). This specific form of PRA is an autosomal recessively inherited, late-onset retinal degenerations affecting several different breeds of dog (Aguirre and Acland, 1988).

Mutations at the prcd 'gene locus account for all of the autosomal recessive late-onset hereditary retinal degenerations recognized to date in dogs. By cross-breeding experiments, it has been determined that the prcd gene locus is responsible for progressive retinal atrophy in poodles (toy, and miniature), cocker spaniels (American, and English), Labrador retrievers, and Portuguese water dogs (see, e.g., Aguirre and Acland, 1988, Aguirre and Acland, 1991; Pearce-Kelling et al., 2002). Cross-breeding experiments suggest the same mutation in the F04 gene (which is gene responsible for prcd) is also present in several other breeds either in dogs affected with prcd; or carriers of the disorder. However, based on clinical and genetic parameters consistent with disease caused by mutations at the prcd gene locus, other breeds of dogs suspected of having prcd as the form of observed progressive retinal atrophy include akita, basenji, border collie, English mastiff, English springer spaniel, Havanese, lowchen, samoyed, standard wirehaired dachshund, Tibetan terriers, Bernese mountain dog, and miniature schnauzer. Depending on the breed of the dog, different mutations responsible for allelic variants of the prcd gene locus can regulate the rate of progression, but not the phenotype, of photoreceptor degeneration.

Clinical diagnosis of prcd disease is complicated by the need for sophisticated testing methods such as ERG, and by the late onset of the disease. The age at which the disease can be diagnosed by current methods may be past the dog's reproductive life. For example, in English cocker spaniels, progressive retinal atrophy may be diagnosed by ERG at three years of age, and by ophthalmoscopy at 5-8 years of age. This late age of diagnosis results in the dissemination of the undesirable trait within the population, and an increase in the disease frequency.

The estimated prevalence of progressive rod-cone degeneration differs among affected breeds. It is believed that approximately 2% of Labrador retrievers more than 2 to 3 years old are affected with progressive rod-cone degeneration; if so, then the proportion of Labrador retrievers expected to be heterozygous at the prcd locus could be as high as 24%. In poodles and cocker spaniels, the disease rate is higher than that observed in Labrador retrievers, and hence, the carrier rate would be expected to be higher. From the results of a survey of Portuguese water dogs, the calculated carrier frequency is approximately 40%.

Traditional measures for controlling inherited diseases in a population included performing "test" matings to identify carrier dogs, and to eliminate the identified carriers from breeding programs, thereby reducing the frequency of genetic disease in a breed. In a test mating, the dog being evaluated as a potential carrier of the genetic disease is mated with a dog known to be affected with the disease. Progeny are then observed for absence or presence of the disease, and a litter equal to or larger than 6, all of which are unaffected offspring, typically "clears" the dog from being a carrier. While test matings have been effectively used for breeds having large litter sizes, and for diseases which are early onset, such a procedure is not practical for reducing the frequency of prcd. In addition to the disadvantages of test matings such as great expenses in time and effort incurred to clear a dog and that affected dogs can be born if the dog to be evaluated is a carrier, test matings are not particularly suited for detection of carriers of prcd because of the late onset of clinical symptoms associated with the disease, and because some of the breeds affected have small litters (too small for establishing statistical probability).

Although the gene carrying the mutation or mutations that cause prcd has previously been unknown, genetic linkage studies in prcd families have shown that the gene that causes the disease in dogs resides on the centromeric end of canine chromosome 9, an area that is homologous to the telomeric end of the long arm of human chromosome 17 (Acland et al., 1999; Sidjanin et al., 2003).

In spite of the extensive efforts in the art to find the gene responsible for prcd, until now the gene has remained elusive. Identification, isolation, cloning, and sequencing of the prcd gene would enable the design and manufacture of products useful for the diagnosis and screening for prcd. Therefore, there has been an ongoing need in the canine breeding industry for a genetic test that permits direct identification of dogs that have the prcd form of progressive retinal atrophy (e.g., before detectable onset of clinical symptoms), as well as permitting the genotyping of dogs at risk for prcd to establish if they are affected, carriers or genetically normal.

SUMMARY OF THE INVENTION

The present invention provides an isolated nucleic acid molecule encoding a novel disease-associated canine gene, referred to herein as the F04 gene. The invention further provides the F04 gene having a G to A mutation at position 1298 of SEQ ID NO:1. This transversion is associated with and is indicative of prcd.

The present invention also relates to a method for identifying dogs, which are genetically normal, carriers of, or affected with prcd disease. Genetically normal dogs are those in which both alleles of the F04 gene have G as the nucleotide at a position corresponding to nucleotide position 1298 of SEQ ID NO:1. Affected dogs or predisposed dogs are those in which both alleles of the F04 gene have A as the nucleotide at a position corresponding to nucleotide position 1298 of SEQ ID NO:1. Carrier dogs are those in which one allele of the F04 gene has G and the other allele has A as the nucleotide at a position corresponding to nucleotide position 1298 of SEQ ID NO:1. A change of G to A in the F04 gene at a position corresponding to nucleotide position 1298 of SEQ ID NO:1 is termed herein as the "prcd mutation". The nucleotide position 1298 in SEQ ID NO:1 also corresponds to nucleotide position 115 in the cDNA sequence shown in SEQ ID NO:3

The method comprises the steps of obtaining a biological sample from a dog and testing the biological sample to identify whether or not G is present at a position corresponding to nucleotide position 1298 of the F04 gene. In one embodiment, the method comprises detecting a G to A mutation at a position corresponding to nucleotide position 1298 of SEQ ID NO:1 in one or both alleles which is indicative of a dog that is a carrier of or a dog that is affected with (or predisposed to prcd respectively.

The present invention also provides a method for selecting dogs for breeding. This method comprises obtaining a biological sample from a dog, testing the biological sample for the F04 gene having a prcd mutation in one or both alleles, and eliminating dogs with the prcd mutation from a breeding stock, or breeding the dogs with the prcd mutation with genetically normal dogs.

BRIEF DESCRIPTION OF THE FIGURES

FIG. 1 shows the genomic sequence of the canine F04 gene.

FIG. 2 shows the sequence of the cDNA from the canine F04 gene.

FIG. 3 is a representation of restriction endonuclease digestion of amplified products from genetically normal, carrier dogs or dogs affected with prcd.

DESCRIPTION OF THE INVENTION

Figures 3A, 3B:
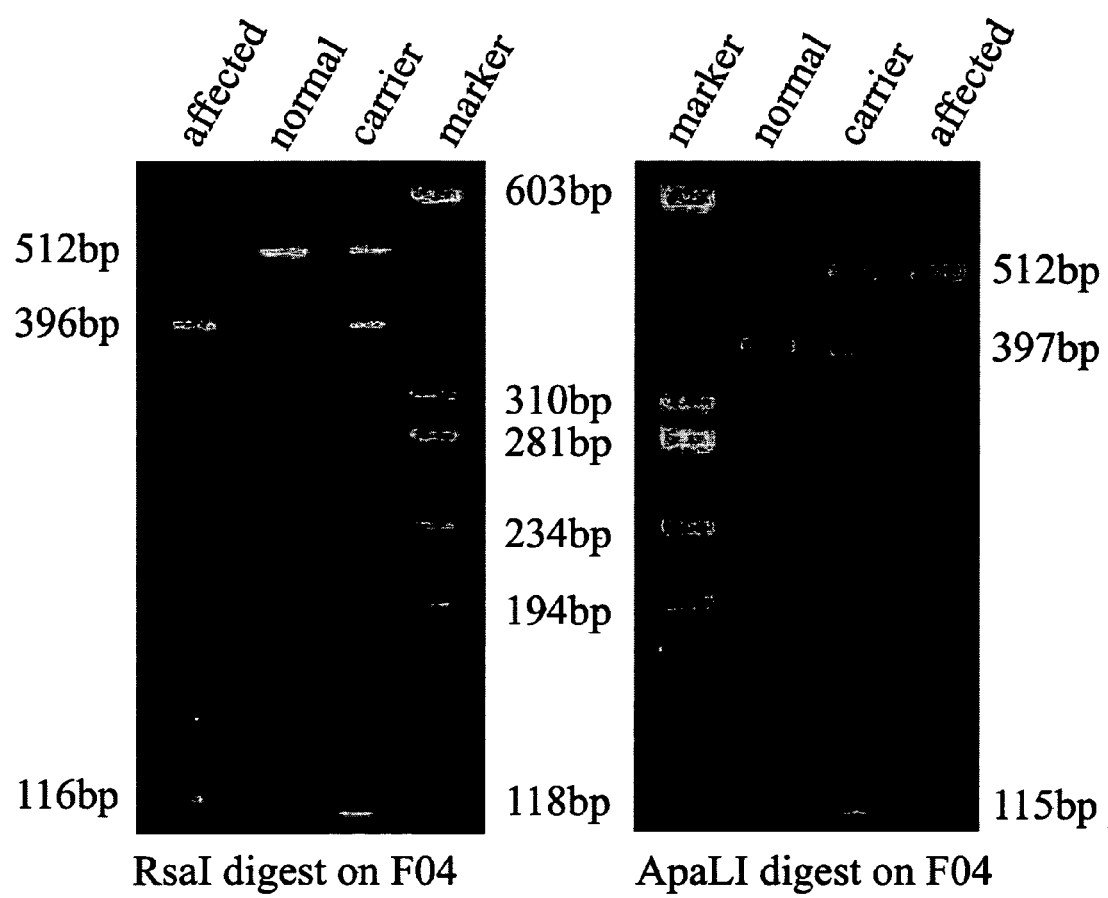
FIG. 3A shows digestion with the restriction endonuclease RsaI and FIG. 3B shows digestion with restriction endonuclease ApaLI.

This invention provides a nucleic acid molecule encoding a novel F04 gene located on chromosome 9 in dogs. The sequence of the wild type F04 gene is presented in FIG. 1 and details pertaining to the sequence are as follows.

Explanation of the Genomic Sequence

The genomic sequence of the F04 gene is 18592 bp long. The sequence listed in SEQ ID NO:1 includes, all polymorphisms identified heretofore. Nucleotide exchanges are shown in italics as follows: W=A/T; M=A/C; R=A/G; Y=C/T; S=C/G; K=G/T. Insertion/deletions are shown in italics and underlined. Sequence for the affected and alternative allele for all polymorphisms shown in the sequence are presented in a separate Polymorphism table (Example 2). Microsatellite at position 13,146-13,278 bp is also shown in italics and is boxed.

In the public domain canine genome sequence assembly (canFam1) dated July 2004 (http://genome.ucsc.edu/cgi-bin/hgTracks?org-Dog&db=canFam1&hgsid=42443361), the F04 genomic sequence (SEQ ID NO:1) is localized incorrectly to chr18:26,568,308-26,586,788. We believe this is incorrect, as we have established through our BAC contig, and by FISH and meiotic linkage mapping that, as predicted by comparison to the homologous regions of the human and mouse genomes, this canine genomic region is properly located on CFA9. This discrepancy does not affect the accuracy or the utility of the tests described herein.

Throughout this sequence, proposed exons and UTR regions are shown in upper case letters and defined exons are bolded. Intronic regions are in lower case letters.

Exon 1: bp 1-1,367

Includes a TATA box at position 727-731, three CRX binding sites at positions 1,122-1,128; 1,159-1,165; 1,177-1,183 and the ATG signal indicating the start of the ORF at position 1,294-1,296 all underlined and boxed.

The prcd mutation at position 1,298 is shown in italics, bold and boxed. The mutation is a change of G to A and is shown as "R".

Exon 2: bp 1,650-1,718
Exon 3: bp 3,746-3,826

Includes the stop codon at position 3,765-3,767 shown underlined and boxed.

Exon 4: bp 4,161-4,256
3'UTR: bp 4,257-18,592

Within this region there are several potential adenylation signals which are pointed out underlined and boxed. The region entitled 3'UTR has also been shown to contain regions of alternative splicing (indicated in bold), which further defines within this region:

Exon 5a: bp 4,806-5,399
Exon 5b: bp 4,839-5,399
Exon 5c: bp 5,093-5,399
Exon 6: bp 6,558-6,665
Exon 7: bp 6,927-7,164
Exon 8: bp 7,547-7,720
Exon 9: bp 12,275-18,592

The deduced amino acid sequence of a putative protein encoded by the F04 gene, based on the sequence of SEQ ID NO:1, and assuming a start site at position 1294 is shown below as SEQ ID NO:2.

(SEQ ID NO:2)
Met Cys Thr Thr Leu Phe Leu Leu Ser Thr Leu Ala

Met Leu Trp Arg Arg Arg Phe Ala Asn Arg Val Gln

Pro Glu Pro Ser Gly Ala Asp Gly Ala Val Val Gly

Ser Arg Ser Glu Arg Asp Leu Gln Ser Ser Gly Arg

Lys Glu Glu Pro Leu Lys

In this case, the prcd mutation would result in cysteine (the 2nd amino acid) being replaced by tyrosine.

The F04 cDNA Sequence (See SEQ ID NO:3)

Several splice variants of the F04 gene have been identified, all of which include the same ORF. The shortest full length splice variant is 695 bp long; the cDNA (SEQ ID NO:3) for this variant of the F04 gene is shown in FIG. 2. Those skilled in the art will recognize that potential future identification of additional exons, that do not alter the F04 ORF as described herein (such as a noncoding exon 5' to exon 1, or 3' to exon 3), will not affect the demonstrated association of the prcd mutation with PRA or detection of the prcd mutation as described herein.

Explanation of the cDNA Sequence:

The cDNA sequence embeds the ORF of 165 bp, located at position 111-275 (both start and stop codon are highlighted in bold). The mutation is located within the ORF at position 115 shown in italics, bold and boxed (Normal allele=G; mutant allele=A). Other polymorphisms (for examples: Y=C/T, nt 312 SEQ ID NO:3, Polymorphism# 55, Table 1; and R=G/A, nt 633 SEQ ID NO:3, Polymorphism# 57, Table 1) in the 3'UTR are not disease associated because both alleles have been identified on normal chromosomes. All cDNAs that include the F04 ORF incorporate exon 1 (bp 1-184), exon 2 (bp 185-253), exon 3 (bp 254-334) and exon 4 (bp 335-695), however, partial cDNAs obtained using different primer sets establish that different splicing variants in the 3'UTR can include at least exons 5 and 8 as defined in the genomic sequence. Other features are the same as in the genomic DNA.

Detection of the prcd mutation in the F04 gene can be carried out in any suitable biological sample obtained from a dog. In a preferred embodiment, the biological sample is any tissue containing genomic DNA. Suitable sources of biological sample include blood, hair, mucosal scrapings, semen, tissue biopsy, or saliva. In one embodiment, the biological sample is blood.

Dogs carrying the prcd mutation in F04 gene may be detected by testing either the DNA or the RNA, using a variety of techniques that are well known in the art. The genomic DNA used for the diagnosis may be obtained from a biological sample as described above. The DNA may be used directly or may be amplified enzymatically in vitro through use of PCR (Saiki et al., Science, 239:487-491 (1988)) or other in vitro amplification methods such as the ligase chain reaction (LCR) (Wu and Wallace, Genomics, 4:560-569 (1989)), strand displacement amplification (SDA) (Walker et al., PNAS USA, 89:392-396 (1992)), self-sustained sequence replication (3SR) (Fahy et al., PCR Methods Appl., 1:25-33 (1992)), prior to mutation analysis. The methodology for preparing nucleic acids in a form that is suitable for mutation detection is well known in the art.

Detection of DNA sequence mutations, such as the prcd mutation in the F04 gene, can be accomplished by a variety of methods including, but not limited to, restriction-fragment-length-polymorphism detection based on allele-specific restriction-endonuclease cleavage (Kan and Dozy Lancet, 2(8096):910-912 (1978)), hybridization with allele-specific oligonucleotide probes (Wallace et al., Nucl Acids Res., 6:3543-3557 (1978)) including immobilized oligonucleotides (Saiki et al., PNAS USA, 86:6230-6234 (1989)) or oligonucleotide arrays (Maskos and Southern, Nucl Acids Res., 21:2269-2270 (1993)), allele-specific PCR (Newton et al., Nucl Acids Res., 17:2503-25 16 (1989)), mismatch-repair detection (MRD) (Faham and Cox, Genome Res., 5:474-482 (1995)), denaturing-gradient gel electrophoresis (DGGE) (Fisher and Lerman et al., PNAS USA., 80:1579-1583 (1983)), single-strand-conformation-polymorphism detection (Orita et al., Genomics, 5:874-879 (1983)), RNAase cleavage at mismatched base-pairs (Myers et al., Science, 230:1242 (1985)), chemical (Cotton et al., PNAS USA, 85:4397-4401 (1988)) or enzymatic (Youil et al., PNAS USA, 92:87-91 (1995)) cleavage of heteroduplex DNA, methods based on allele specific primer extension (Syvanen et al., Genomics 8:684-692 (1990)), genetic bit analysis (GBA) (Nikiforov et al., Nucl Acids Res., 22:4167:-4175 (1994)), the oligonucleotide-ligation assay (OLA) (Landegren et al., Science, 241:1077 (1988)), the allele-specific ligation chain reaction (LCR) (Barrany, PNAS USA, 88:189-193 (1991)), gap-LCR (Abravaya et al., Nucl Acids Res., 23:675-682 (1995)), and radioactive and/or fluorescent DNA sequencing using standard procedures well known in the art.

Further, several new techniques have been described including dynamic allele-specific hybridization (DASH), microplate array diagonal gel electrophoresis (MADGE), Pyrosequencing™, the TaqMan system as well as various DNA "chip" technologies such as the Affymetrix polymorphism chips. These methods require amplification of the target genetic region, typically by PCR. Still other newly developed methods, which may not need PCR are based on the generation of small signal molecules by invasive cleavage followed by mass spectrometry or immobilized padlock probes and rolling-circle amplification. Several of the methods known in the art for detecting specific single nucleotide polymorphisms are described in U.S. Pat. No. 6,720,141 and the description of these methods is incorporated herein by reference.

As will be appreciated, the mutation analysis may also be performed on samples of RNA by reverse transcription into cDNA therefrom.

Any one or any combination of such techniques can be used in accordance with the invention for the design of a diagnostic device and method for the screening of samples of DNA or RNA for prcd gene mutation of G to A at a position corresponding to nucleotide position 1298 of SEQ ID NO:1 of the F04 gene. Thus, in accordance with the invention, there is provided a nucleic acid based test for prcd gene mutation which comprises providing a sample of a dog's DNA or RNA and assessing the DNA or RNA for the presence of the prcd mutation. Samples of dog DNA or RNA (or genomic, transcribed, reverse transcribed, and/or complementary sequences to the prcd gene) can be readily obtained. Through the identification and characterization of the F04 gene as taught and disclosed in the present invention, one of ordinary skill in the art can readily identify the genomic, transcribed, reverse transcribed, and/or complementary sequences to the prcd gene sequence in a sample and readily detect differences therein.

Accordingly, in one embodiment, the present invention provides nucleic acid fragments for detection of nucleic acids wherein the mutation is present. In general, the detection methods are based on DNA hybridization techniques, wherein hybridization to DNA sequences is performed under stringent conditions such that a change in one nucleotide can be detected. Optimal stringency is normally obtained by adjusting the reaction temperature and/or salt concentration so that the probe will only hybridize to its specific target, although those skilled in the art will recognize that alternative methods of optimizing for target specific hybridization are readily available.

Thus, allele-specific probes can be hybridized under conditions that are sufficiently stringent so that there is a significant difference in the intensity of the two alleles. Preferably, the hybridization conditions are sufficiently stringent so as to produce an essentially binary response (i.e., the probe hybridizes to one but not the other allele).

Further, primers can be designed which hybridize to a target sequence such that upon amplification, products are generated which contain the prcd mutation site. The primers should be long enough to be useful in reactions such as polymerase chain reaction (PCR) process or as probes in a ligase chain reaction (LCR) procedure. Generally fragments which are at least twelve bases in length are considered suitable for amplification reactions. The amplification products can be subjected to restriction endonuclease treatment and identified by denaturing gradient gel electrophoresis so as to distinguish between the amplification products from the two alleles.

Suitable fragments useful for hybridization can be identified from the sequence of the F04 gene presented herein or may be identified by hybridization to the nucleic acid sequence of the F04 gene (SEQ. ID. NO:1) or the cDNA (SEQ ID NO:3) under stringent conditions as described above.

By using the tools and method described herein, dogs which are genetically normal for the disease (G in both alleles), carriers of the prcd disease (G to A transversion in one allele) and dogs which are affected by (or predisposed to) progressive rod-cone degeneration (G to A transversion in both alleles) can be identified. Upon identification, such affected (or predisposed) or carrier dogs can be eliminated from the breeding stock. Alternatively, dogs which are affected (or predisposed) with prcd, or carriers of the prcd disease, can be mated with genetically normal (without the G to A transversion) dogs to ensure the absence in the litter of dogs affected with prcd.

This invention can be used for any breed of dog including, but not limited to, akita, American cocker spaniel, American eskimos, Australian cattle dog, Australian stumpy tailed cattle dog, basenji, Bernese mountain dog, border collie, Chesapeake bay retriever, Chinese crested, English cocker spaniel, English mastiff, English springer spaniel, Entlebucher mountain dog, Finnish lapphund, German shorthaired pointer, giant schnauzer, Havanese, Labrador retrievers, lowchen, miniature poodle, miniature schnauzer, Nova scotia duck tolling retriever, Portuguese water dogs, samoyed, silky terrier, spitz, standard poodle, standard wirehaired dachshund, Tibetan terriers, toy poodle. Because the identical prcd mutation in the F04 gene has been demonstrated to be present in, and cause PRA in so many different breeds, this mutation appears to have arisen long before the differentiation of the dog population into these different breeds. It is thus expected that the same mutation will prove to be present in other breeds of dogs in which its presence is not currently recognized.

The invention will be further understood by the following examples, which are intended to be illustrative and not restrictive in any way.

EXAMPLE 1

We have produced a retina specific canine EST library from 16 week old beagles. One set of 5 individual overlapping EST clones formed a contig which mapped to the previously specified CFA9 area (Sidjanin et al., 2003) and was therefore further investigated. This sequence contained the later defined F04 exon 8 (see below, EST clone contig, 1085 bp).

From sequence information from the above EST contig, and that of hypothetical human genes located within the corresponding region of the human genome sequence as deposited in GenBank, two primers were designed for RT-PCR: Forward: 5'-caccttggccatgctctggc-3' (located at the end of exon 1)—SEQ ID-NO:4 Reverse: 5-aatg-catataaataaagcacttggc-3' (located in exon 8)—SEQ ID NO:5

RT-PCR was performed from a 3.3 week normal dog resulting in a 707 bp product (clone 9) spanning the end of exon 1, exon 2, exon 3, exon 4 and exon 8.

Comparative in silico analysis of canine genomic sequence from our BAC contig (see example 2, below), with public domain human and mouse genomic sequence, identified a highly conserved region, contiguous with the 5' end of clone 9, that included potential CRX binding sites followed by an ATG translation initiation codon immediately upstream to the sequence of clone 9, and predicted an ORF commencing with this ATG and ending with a stop codon in exon 3. This ORF sequence did not correspond to that of any known gene in Genbank, nor did its putative translation share recognizeable domains with or sequence similarity to any other known protein in Genbank.

Because the F04 clone was identified from our retina-specific library, these data combined indicated that the ORF corresponding to F04 represents a novel, previously unrecognized, retina expressed gene. The presence of binding sites for the CRX photoreceptor-specific transcription factor, and the highly conserved structure of the region 5' to the identified start codon identified the putative exon 1 as the first coding exon of a retina-expressed gene. Based on this information a new primer set was designed to include the potential start codon and span exons 1-4:

```
                                          SEQ ID NO:6
Forward: 5'-ccagtggcagcaggaacc-3'  (5' of exon 1)

SEQ ID NO:7
Reverse: 5'-ccaagccagggcatgagc-3'  (3' of exon 4)
```

RT-PCR was performed on both, an 10.4 week normal animal and an 8.6 weeks prcd affected individual resulting in a 562 bp product in both animals (see below, RT-PCR exon 1-4). The only difference observed was a G to A change observed in the affected individual which consequently was identified as the prcd mutation.

To identify the 5' and 3' ends of this gene, we created a 5' RACE retina library from a 10 week old normal dog and a 8 week old affected dog. Amplification of the 5' ends was done with different specific primers located in exon 1 (CCAAGGTGCTGAGTAGGAAGAGGGTGGTG—SEQ ID NO:8). or exon 3 (AGTCCCTGGGGCCGAGCTCCGC-CTGAC—SEQ ID NO:9). Amplification of the 3' ends was done using a specific primer located on exon 1 (CACCAC-CCTCTTCCTACTCAGCACCTTGG—SEQ ID NO:10)—which is the exact complement sequence of the specific primer that is used to run the 5' RACE. Seminested PCR was done with a primer located on exon 3 (AGGGACTGGGAT-CAGCTGGCAGAGGCAG—SEQ ID NO:11) to verify specificity of the product.

The consensus sequence from these experiments is the clone we consider as the cDNA for the F04 gene (see Seq ID No:3) which is shown in FIG. 2. Details of the cDNA sequence are provided above.

To validate the consensus sequence predicted from the 5' and 3' RACE, two primers were used to amplify the consensus sequence from affected and non-affected retina cDNA.

5'- AGTGGCAGCAGGAACCTCAGG- 3'            SEQ ID NO: 29

5'- GGATTATATTAGGGATGAATGAGAAG- 3'       SEQ ID NO: 30

Since the results of a 5' RACE and a 3' RACE are independent results this step is necessary to prove that this transcript is present in the affected and non-affected Retina. The RT-PCR confirmed the presence of such transcript.

By the method described above, the following sequences were obtained.

EST Clone Contig:

The clones originally contained in the EST library produced the following consensus sequence from 5 clones; 1085 bp:.

SEQ ID NO:12
GAGCAGCTGCAGCAGCTGCCACTGCCCTGTGTCACCCCAGGGTGCAAATG

CCACCACGGGGAGCACCCCGCCCATCCCGAACTGTGTGGCTGTGCAGATG

CGGGCAGGATGGTCCTGGGCACAGGCCTTGGTCCAAGACCAGGCAGGCGT

GGTACTTGATCTGAGGTGGGCATCATGGCACAGGAGCTGGTCCCAGGGGT

GCCCGGGGACCTTTATAGAACCTCAGTCGGGAAGAAGCCCAAGACCTTGA

GCCAGAGGGAAGTAATGCTTCTTTGTGAGCCTCAAAAGGAGGGAAATGGC

CAAGGTTTACAGTAATATAATGACACTAATATTATTATTAATAATGGCTA

ATGTGTCTCAAACGCTTCTTACGTGCTAGGCGCTGTGCCAAGTGCTTTAT

TTATATGCATTGTCTCATTTATGGGGCAGGAACTGTTGTCAGTCTCATTT

ACCCAATAAGGAAAGTGCTTGCTCAAGGTCACCCACAGTGAGTAGTGAAG

CCAGGACGTGTTCCCCGGCAAGGTGATGTAAAAGCCTGTGAAGGTATTGG

GCCTCGAGGACATCCTGGGAGTGTGACCTGTCCACCAGGGCACAGGGCAT

GAGAGCTGGCAACCCTCCCTGGTGATACTGCCGCTGCTCAGTCTGCAGAA

ACTCATCATTCCAGGCTGGACCAGACTCTGGGCCCCGAGGGCAGTGACCA

GAGCCACCTTTCCAGGATCTGTCATGCTCCTCAGGGAGGAAGCAGTGGCC

ACTGGCAGGGATGACAGATATCAAGGTTGTCACTCATTGCTGCTGTTGCT

CTGCTGTTTCCTCCAACCAGGGGCAGAGCCCTGGGGGTAAGGGAGGGTGG

CAGCCAGCAGCCCAGCCAGAGAAGGAGGAGCCAGAGGAGGAAGGCTTTGT

TGTTTGTTTTTACAGGGGGACGGTGCAGGGCTTTAAGGAGGTGGCTTCAA

GACCTGCTGACTTTAGCCATAAACTGGTACCTAAGGGTGCTGGACCCTCT

CTGTGGGATACATATGCCCCCTAGTGGGGATTAAGCCTGGAGGGTGGCTG

AG:AAATTAAAGCAAAAAAAAAAAAAAAAAAAAAA

Clone9:

Produced by RT-PCR using primers from exon 8 and the end of exon 1 (707 bp):

SEQ ID NO:13
CACCTTGGCCATGCTCTGGCGCCGCCGGTTCGCCAACCGGGTCCAACCGG

AGCCCAGCGGAGCAGACGGGGCAGTCGTGGGCAGCAGGTCGGAGAGAGAC

CTCCAGTCCTCGGGCAGAAAGGAAGAGCCTCTGAAGTAAGTCTTCACCCG

GTCAGGCGGAGCTCGGCCCCAGGGACTGGGATCAGCTGGCAGAGGCAGTT

CAAGTCCCGGCTGGCCTCTTACCCACAAAGCATGCTGTGGTGGAAGCAGC

AGCAGCAGCAAGAAGAAAAATGGGAAAAAGCAGTCATCAAGAAGGTAGAC

TCCTCCCTTTGAGTCCCTGGACCTGCCTGGCCTCCCTTTGCCCCAGACCC

TGGTGGTGGGGCTCCTGAAGCAAGGCCTGGCTGGGGCAGGCTGGAGGGCA

AAGACGCTCATTGCCCTGGCTTGGGCTCCCTTCCTCTGAGATCCTGAGGA

TAGTCTGAGGCAGGCCCAGAGAGGGACTCAGGTTTCTTATGGAAGGRCTT

CTCATTCATCCCTAATATAATCCTTGCAATGACCCCAAGACCTTGAGCCA

GAGGGAAGTAATGCTTCTTTGTGAGCCTCAAAAGGAGGGAAATGGCCNAG

GNTTACAGTAATATAATGACACTAATATTATTATTAATAATGGCTAATGT

GTCTCAAACGCTTCTTACGTGCTAGGCGCTGTGCCAAGTGCTTTATTTAT

ATGCATT

RT-PCR Exons 1-4

This sequence was created from RT-PCR to compare the ORF of affected and non-affected animals (562 bp):

SEQ ID NO:14
CCAGTGGCAGCAGGAACCTCAGGATGGGCAGCAGTGGCTTGTGAGAGCCG

GCAGGGCCATTTTGGCCTTTCTCCTGCAGACTCTGTCCGGGAGGGGATGG

GGCAGCTGAGCCATGTRCACCACCCTCTTCCTACTCAGCACCTTGGCCAT

GCTCTGGCGCCGCCGGTTCGCCAACCGGGTCCAACCGGAGCCCAGCGGAG

CAGACGGGGCAGTCGTGGGCAGCAGGTCGGAGAGAGACCTCCAGTCCTCG

GGCAGAAAGGAAGAGCCTCTGAAGTAAGTCTTCACCCGGTCAGGCGGAGC

TCGGCCCCAGGGACTGGGATCAGCTGGCAGAGGCAGTTCAAGTCCCGGCT

GGCCTCTTACCCACAAAGCATGCTGTGGTGGAAGCAGCAGCAGCAGCAAG

AAGAAAAATGGGAAAAAGCAGTCATCAAGAAGGTAGACTCCTCCCTTTGA

GTCCCTGGACCTGCCTGGCCTCCCTTTGCCCCAGACCCTGGTGGTGGGGC

TCCTGAAGCAAGGCCTGGCTGGGGCAGGCTGGAGGGCAAAGACGCTCATT

GCCCTGGCTTGG.

The F04 mutation is bolded and presented as a G in normal and an A in prcd affected dogs.

Splice Variants

In addition to alternative splicing observed in some of the sequences obtained throughout the cloning process of the F04 gene (described above), different splice variants were identified using RT-PCR with primers located in exons 2 and 3, and with primers located in downstream predicted exons (see below).

Clone 1:

RT-PCR was performed using a primer from exon 3 (CAGTCGTGGGCAGCAGGTCGG—SEQ ID NO:15) and one from exon 8 (AATGCATATAAATAAAGCACT-TGGC—SEQ ID NO:16) producing a 316 bp product:

SEQ ID NO:17
CAGTCGTGGGCAGCAGGTCGGAGAGAGACCTCCAGTCCTCGGGCAGAAAG

GAAGAGCCTCTGAAGTAAGTCTTCACCCGGTCAGGCGGAGCTCGGCCCCA

GGGGTGCCCGGGGACCTTTATAGAACCTCAGTCGGGAAGAAGCCCAAGAC

CTTGAGCCAGAGGGAAGTAATGCTTCTTTGTGAGCCTCAAAAGGAGGGAA

ATGGCCAAGGTTTACAGTAATATAATGACACTAATATTATTATTAATAAT

GGCTAATGTGTCTCAAACGCTTCTTACGTGCTAGGCGCTGTGCCAAGTGC

TTTATTTATATGCATT.

Primers from exon 2 (GCAGCAGGTCG-GAGAGAGAC—SEQ ID NO:18) and exon 5 (CTTCCCT-CAGATGTGGAGTCAG—SEQ ID NO:19) were used to amplify cDNA obtained from normal and affected retina. Three different products were obtained as shown below.

Product Number 1:

SEQ ID NO:20
GCCACCGGGTCCACCGGAGCCCAGCGGAGCAGACGGGGCAGTCGTGGGCA

GCAGGTCGGAGAGAGACCTCCAGTCCTCGGGCAGAAAGGAAGAGCCTCTG

AAGTAAGTCTTCACCCGGTCAGGCGGAGCTCGGCCCCAGGGACTGGGATC

AGCTGGCAGAGGCAGTTCAAGTCCCGGCTGGCCTCTTACCCACAAAGCAT

GCTGTGGTGGAAGCAGCAGCAGCAGCAAGAAGAAAAATGGGAAAAAGCAG

TCATCAAGAAGTTTCCAGGGCACTTGCCTCTCCCCGGTCCCCAGAGCTCA

CCCCGTCACCAGCCACTCTGCTGCAGTTCTCAATAAGAAATGCCAGCTGG

GATCTGTGACATGTCTGCCTGCGGCTGGAAGGAAGCATCTCTCAACCTGT

CCTCTGAGCGTGTCTGCGTGCCTGTGTGCATGCGTGCGTGTGTTCCAAAG

GGGCAGTCGCATGTGGGAAGGGAAGAAGCCTGACACTTGTTCTTGTCAAT

CTGCTGACTGCTCAGTACCACGGCGGCTCTGCCATTTCTCCCTCACAGTC

CTGCTCGACCCAGAGCAGAGATCAAAGCAGATTTCCGCTTCTGCTCCCTG

AGATCCAGGCGCAGACCTGCAGGCAGCTGCTCCCCACTGTCTGGAAGCCA

TTCATCATGCAAAGCGCCTCCCCACCAAACCCCTGCCTGCACGTGCATCG

TCCCCCCACCATCACCATCCAGCCCCAGGGTGGGCAGGGAGGTCCCTGCC

CTAGCTGCACACCCCCAGGCCATCAAGAGGCAGGAGATGGGGAGT.

Product Number 2:

SEQ ID NO:21
GCCACCGGGTCCACCGGAGCCCAGCGGAGCAGACGGGGCAGTCGTGGGCA

GCAGGTCGGAGAGAGACCTCCAGTCCTCGGGCAGAAAGGAAGAGCCTCTG

AAGTAAGTCTTCACCCGGTCAGGCGGAGCTCGGCCCCAGGGACTGGGATC

AGCTGGCAGAGGCAGTTCAAGTCCCGGCTGGCCTCTTACCCACAAAGCAT

GCTGTGGTGGAAGCAGCAGCAGCAGCAAGAAGAAAAATGGGAAAAAGCAG

TCATCAAGAAGAGCTCACCCCGTCACCAGCCACTCTGCTGCAGTTCTCAA

TAAGAAATGCCAGCTGGGATCTGTGACATGTCTGCCTGCGGCTGGAAGGA

AGCATCTCTCAACCTGTCCTCTGAGCGTGTCTGCGTGCCTGTGTGCATGC

GTGCGTGTGTTCCAAAGGGGCAGTCGCATGTGGGAAGGGAAGAAGCCTGA

CACTTGTTCTTGTCAATCTGCTGACTGCTCAGTACCACGGCGGCTCTGCC

ATTTCTCCCTCACAGTCCTGCTCGACCCAGAGCAGAGATCAAAGCAGATT

TCCGCTTCTGCTCCCTGAGATCCAGGCGCAGACCTGCAGGCAGCTGCTCC

CCACTGTCTGGAAGCCATTCATCATGCAAAGCGCCTCCCCACCAAACCCC

TGCCTGCACGTGCATCGTCCCCCCACCATCACCATCCAGCCCCAGGGTG

GGCAGGGAGGTCCCTGCCTAGCTGCACACCCCCAGGCCATCAAGAGGCA

GGAGATGGGGAGT.

Product Number 3:

SEQ ID NO:22
GCCACCGGGTCCACCGGAGCCCAGCGGAGCAGACGGGGCAGTCGTGGGCA

GCAGGTCGGAGAGAGACCTCCAGTCCTCGGGCAGAAAGGAAGAGCCTCTG

AAGTAAGTCTTCACCCGGTCAGGCGGAGCTCGGCCCCAGGGACTGGGATC

AGCTGGCAGAGGCAGTTCAAGTCCCGGCTGGCCTCTTACCCACAAAGCAT

GCTGTGGTGGAAGCAGCAGCAGCAGCAAGAAGAAAAATGGGAAAAAGCAG

TCATCAAGAAGTCCTGCTCGACCCAGAGCAGAGATCAAAGCAGATTTCCG

CTTCTGCTCCCTGAGATCCAGGCGCAGACCTGCAGGCAGCTGCTCCCCAC

TGTCTGGAAGCCATTCATCATGCAAAGCGCCTCCCCACCAAACCCCTGCC

TGCACGTGCATCGTCCCCCCACCATCACCATCCAGCCCCAGGGTGGGCA

GGGAGGTCCCTGCCTAGCTGCACACCCCCAGGCCATCAAGAGGCAGGAG

ATGGGGAGT.

RT-PCR was done on affected and non-affected retina using the following primers:

```
5'- TTAATCAGTCTGCACAAGGTCG- 3'      SEQ ID NO: 31
5'- GGGTCATTGCAAGGATTATATTAGG- 3'   SEQ ID NO: 32
```

Two splice variants were observed:

Product Number 1:

SEQ ID NO: 33
TTAATCAGTCTGCACAAGGTCGGGTTGGCTGACCCCACTAATCAGCTTGA

GCCTCCTAATCCAGTGGCAGCAGGAACCTCAGGATGGGCAGCAGTGGCTT

GTGAGAGCCGGCAGGGCCATTTTGGCCTTTCTCCTGCAGACTCTGTCCGG

GAGGGGATGGGGCAGCTGAGCCATGTRCACCACCCTCTTCCTACTCAGCA

CCTTGGCCATGCTCTGGCGCCGCCGGTTCGCCAACCGGGTCCAACCGTGA

GAAGCTGATGGGCCATGGGCAGGGATGGGGAGAGGAGAAGCTAGGGG

GTGAGGGGTGGTGCAGGGGCTGCCTGGACCTCCTGGGAGGCTGGAGGGCG

GGGAGGATTTGCAGGGAGGTCCAGAGAGGTTTCCCATCAGAGCACGCGGG

GGCGGGGGCTCGCAGGTGCTCCGAGACTGGCTGGAGTCCCCGGTCCCCCA

GCCCAACACGGCCAGGAGAGGGGGTTCTGGGCCCGGGCGCTGCCCACAGC

-continued

TCTTCCAGCCTCTTCCTCCCGCCCACAGGGAGCCCAGCGGAGCAGACGGG

GCAGTCGTGGGCAGCAGGTCGGAGAGAGACCTCCAGTCCTCGGGCAGAAA

GGAAGAGCCTCTGAAGTAAGTCTTCACCCGGTCAGGCGGAGCTCGGCCCC

AGGGACTGGGATCAGCTGGCAGAGGCAGTTCAAGTCCCGGCTGGCCTCTT

ACCCACAAAGCATGCTGTGGTGGAAGCAGCAGCAGCAGCAAGAAGAAAAA

TGGGAAAAAGCAGTCATCAAGAAGGTAGACTCCTCCCTTTGAGTCCCTGG

ACCTGCCTGGCCTCCCTTTGCCCCAGACCCTGGTGGTGGGGCTCCTGAAG

CAAGGCCTGGCTGGGGCAGGCTGGAGGGCAAAGACGCTCATTGCCCTGGC

TTGGGCTCCCTTCCTCTGAGATCCTGAGGATAGTCTGAGGCAGGCCCAGA

GAGGGACTCAGGTTTCTTATGGAAGGGCTTCTCATTCATCCCTAATATAA

TCCTTGCAATGACCC

Product Number 2:

SEQ ID NO: 34
TTAATCAGTCTGCACAAGGTCGGGTTGGCTGACCCCACTAATCAGCTTGA

GCCTCCTAATCCAGTGGCAGCAGGAACCTCAGGATGGGCAGCAGTGGCTT

GTGAGAGCCGGCAGGGCCATTTTGGCCTTTCTCCTGCAGACTCTGTCCGG

GAGGGGATGGGGCAGCTGAGCCATGTRCACCACCCTCTTCCTACTCAGCA

CCTTGGCCATGCTCTGGCGCCGCCGGTTCGCCAACCGGGTCCAACCGGAG

CCCAGCGGAGCAGACGGGGCAGTCGTGGGCAGCAGGTCGGAGAGAGACCT

CCAGTCCTCGGGCAGAAAGGAAGAGCCTCTGAAGTAAGTCTTCACCCGGT

CAGGCGGAGCTCGGCCCCAGGGACTGGGATCAGCTGGCAGAGGCAGTTCA

AGTCCCGGCTGGCCTCTTACCCACAAAGCATGCTGTGGTGGAAGCAGCAG

CAGCAGCAAGAAGAAAAATGGGAAAAAGCAGTCATCAAGAAGGTAGACTC

CTCCCTTTGAGTCCCTGGACCTGCCTGGCCTCCCTTTGCCCCAGACCCTG

GTGGTGGGCTCCTGAAGCAAGGCCTGGCTGGGGCAGGCTGGAGGGCAAA

GACGCTCATTGCCCTGGCTTGGGCTCCCTTCCTCTGAGATCCTGAGGATA

GTCTGAGGCAGGCCCAGAGAGGGACTCAGGTTTCTTATGGAAGGGCTTCT

CATTCATCCCTAATATAATCCTTGCAATGACCC

The above results indicate that there are several retinal splice variants of F04. Based on these splice variants and comparative genomic analysis, the genomic organization of F04 was characterized. However, all splice variants relevant to prcd include exons 1-4 and the shortest and most abundantly expressed such disease-relevant transcript is the cDNA identified as SEQ ID No:3.

EXAMPLE 2

Since mapping the prcd locus to canine chromosome 9 (CFA9), we have mapped the prcd disease interval at higher resolution, narrowed the identified canine genomic region in which the prcd gene is located, and tested all candidate genes within that region. Initially, we created a physical map of the region using canine BACs (Sidjanin, 2003), and identified multiple polymorphic markers within and flanking this region. Examination of genotypes of prcd-affected dogs from multiple breeds for these polymorphic markers established that within breeds the haplotype that cosegregated with the prcd mutation extended across a broad region, including the physically mapped interval (Sidjanin et al., 2003). However, comparison of these genotypes revealed that the breed specific haplotypes varied among breeds within the area initially published (Sidjanin et al., 2003), but was consistent for all breeds for a set of markers physically located within a single BAC clone (BAC #10M13; Li et al, 1999) located adjacent to the area initially published. This BAC clone contained several genes. Single nucleotide polymorphisms were identified for each of these genes, and a single haplotype was constructed which differentiated the prcd-transmitting CFA9 from that of all normal dogs tested (Table 1) in all breeds known to be affected with prcd.

TABLE 1

Linkage disequilibrium (LD) region flanking the canine prcd/F04 gene on canine chromosome 9 (CFA9). All genes in this region are located in canine BAC # 10M13. The "affected allele" for each polymorphism is that found on all examined prcd-transmitting chromosomes from dogs of multiple breeds; the "alternative allele" is that which is present, for example, in BAC # 10M13. Where polymorphism information is bolded, the Polymorphism Name indicates the position (base number) in the F04 genomic sequence (i.e. SEQ ID NO: 1). Polymorphism Location indicates the gene in the genomic sequence of which the polymorphism is located.

| Polymorphism # | Polymorphism Name | Affected allele | Alternative allele | Polymorphism Location |
|---|---|---|---|---|
| 1 |  | A | G | FLJ22341 |
| 2 | p43 | G | T | FLJ22341 |
| 3 |  | C | T | FLJ22341 |
| 4 |  | C | T | FLJ22341 |
| 5 | b712 | A | C | FLJ22341 |
| 6 | b817 | deletion | CTG | FLJ22341 |
| 7 | b1149 | T | C | FLJ22341 |
| 8 | p49 | C | T | FLJ22341 |
| 9 |  | T | G | FLJ22341 |
| 10 | SINE | no SINE | SINE | FLJ22341 |
| 11 | p48 | G | A | FLJ22341 |
| 12 |  | A | G | FLJ22341 |
| 13 |  | A | G | FLJ22341 |
| 14 |  | T | C | FLJ22341 |
| 15 |  | C | T | FLJ22341 |
| 16 | p45 | T | C | FLJ22341 |
| 17 | p41 | C | T | FLJ22341 |
| 18 |  | C | T | FLJ22341 |
| 19 | b682 | C | G | FLJ22341 |
| 20 | b937 | A | G | FLJ22341 |
| 21 | b1130 | A | G | FLJ22341 |
| 22 | b1275 | G | deletion | FLJ22341 |
| 23 | b1351 | G | A | FLJ22341 |
| 24 | p38 | T | C | CYGB |
| 25 |  | G | A | CYGB |
| 26 |  | A | G | CYGB |
| 27 | CYGB | T | C | CYGB |
| 28 | b3128 | T | C | CYGB |
| 29 | b3133 | T | C | CYGB |
| 30 | b3605 | C | G | CYGB |
| 31 | b3769 | C | G | CYGB |
| 32 | 3820-23 | deletion | TGCC | CYGB |
| 33 | p40 | A | G | CYGB |
| 34 |  | G | A | CYGB |
| 35 |  | A | G | CYGB |
| 36 | 31F5 | A | C | CYGB |
| 37 | 31F4 | A | G | CYGB |
| 38 |  | A | G |  |
| 39 | 285 | C | T | F04 |
| 40 | 851 | C | G | F04 |
| 41 | 999 | C | T | F04 |
| 42 | 1298 | A | G | F04 |
| 43 | 1633-1635 | CTT | deletion | F04 |
| 44 | 1854 | deletion | C | F04 |
| 45 | 1912 | C | G | F04 |

TABLE 1-continued

Linkage disequilibrium (LD) region flanking the canine prcd/F04 gene on canine chromosome 9 (CFA9). All genes in this region are located in canine BAC # 10M13. The "affected allele" for each polymorphism is that found on all examined prcd-transmitting chromosomes from dogs of multiple breeds; the "alternative allele" is that which is present, for example, in BAC # 10M13. Where polymorphism information is bolded, the Polymorphism Name indicates the position (base number) in the F04 genomic sequence (i.e. SEQ ID NO: 1). Polymorphism Location indicates the gene in the genomic sequence of which the polymorphism is located.

| Polymorphism # | Polymorphism Name | Affected allele | Alternative allele | Polymorphism Location |
|---|---|---|---|---|
| 46 | 2413 | A | G | F04 |
| 47 | 2590 | T | C | F04 |
| 48 | 2601-2603 | deletion | TCC | F04 |
| 49 | 2607 | A | G | F04 |
| 50 | 2660-2666 | ATGAGAA | deletion | F04 |
| 51 | 2710 | C | T | F04 |
| 52 | 2741 | G | A | F04 |
| 53 | 2769 | C | T | F04 |
| 54 | 3119 | G | A | F04 |
| 55 | 3804 | C | T | F04 |
| 56 | 3971 | G | C | F04 |
| 57 | 4459 | G | A | F04 |
| 58 | 5244 | G | A | F04 |
| 59 | 5698 | G | T | F04 |
| 60 | 6254 | A | C | F04 |
| 61 | 6318 | deletion | G | F04 |
| 62 | 6953 | T | C | F04 |
| 63 | 7030 | T | A | F04 |
| 64 | 7183 | A | C | F04 |
| 65 | 7239 | G | A | F04 |
| 66 | 7855 | A | G | F04 |
| 67 | 8230 | C | T | F04 |
| 68 | 8843 | G | deletion | F04 |
| 69 | 8977 | G | A | F04 |
| 70 | 10230 | A | G | F04 |
| 71 | 10268 | A | C | F04 |
| 72 | 10855 | A | T | F04 |
| 73 | 12175 | A | G | F04 |
| 74 | 12613 | A | G | F04 |
| 75 | 15033 | C | T | F04 |
| 76 | 15347 | G | A | F04 |
| 77 | 15359 | A | T | F04 |
| 78 | 15445 | T | C | F04 |
| 79 | 17200 | T | C | F04 |
| 80 | 17407 | deletion | C | F04 |
| 81 | 17435-17437 | GGG | deletion | F04 |
| 82 | 17672 | T | deletion | F04 |
| 83 | 17892 | A | G | F04 |
| 84 | b1409 | C | T | STHM |
| 85 | P2 | A | C | STHM |
| 86 | STHM-NaeI | A | G | STHM |
| 87 | STHM- AvaI | C | T | STHM |
| 88 | base 3526 | C | T | STHM |
| 89 | base 3655 | G | A | STHM |
| 90 | 10-299 | G | A | STHM |
| 91 | 10-597 | G | G | STHM |
| 92 | b2263 | deletion | T | STHM |
| 93 | b2411 | T | C | STHM |
| 94 | b2425 | deletion | C | STHM |
| 95 | b2748 | G | deletion | STHM |
| 96 | from RT-PCR | A | G | STHM |

For each of these genes the exons were sequenced and examined, and a disease associated sequence change (i.e. a mutation) was found in only one gene. This gene, referred to herein as F04, is located within the interval described in U.S. Pat. No. 5,804,388. Details of the canine cDNA and genomic DNA sequence for F04 have been provided above. The mutation, at nucleotide 1298 of SEQ ID NO: 1 represents a G to A transition, from normal sequence to affected. We refer to this sequence change as the "prcd mutation" in F04 gene herein and is shown as polymorphism no. 42 in the table above.

EXAMPLE 3

This example describes a PCR-based restriction enzyme digestion test developed to identify the sequence change in the F04 gene. The following primers were used:

```
primer 1: ccagtggcagcaggaacc -       SEQ ID NO:27
primer 2: ccgacctgctgcccacgactg -    SEQ ID NO:28
```

PCR is run under standard conditions (annealing temp 58 degree C., 1.5 MgCl2) in 25 microliters, 35 cycles. The amplification product is 512 bp in size (corresponding to bp 1182 to 1693 in SEQ ID NO:1. The restriction enzyme RsaI digests the amplification product bearing the A allele, but not the G allele. Conversely, ApaLI digests the G allele but not the A allele. Both digests were performed at 37° C. for 2 hours.

Restriction digestion thus yields the diagnostic results shown in Table 2:

TABLE 2

| ENZYME (restriction site) | ALLELE | FRAGMENT SIZE(S) (bp) |
|---|---|---|
| RsaI (GT\|AC) | G | 512 |
|  | A | 116; 396 |
| ApaLI (G\|TGCAC) | G | 115; 397 |
|  | A | 512 |

A large population of dogs affected with prcd was examined. We have tested more than 100 affected animals from 13 different breeds or breed varieties. These include: 36 Australian cattle dogs, 2 Chinese crested, 5 English cocker spaniels, 5 Finish Lapphunds, 48 Labrador retrievers, 45 miniature or toy poodles, 1 Nova Scotia duck tolling retriever, 3 Portuguese water dogs, 1 Silky Terrier, 25 American eskimos, and 14 Entlebucher mountain dogs.

An example of the identification of the G allele (normal) and the A allele (affected allele) following RsaI digestion is shown in FIG. 3A and following digestion with ApaLI is shown in FIG. 3B. For the RsaI digestion (FIG. 3A), a normal dog (GG) shows a product of 512 bp, an affected dog (AA) shows products of 396 bp and 116 bp while a carrier dog (AG) shows products of 512 bp, 396 p and 116 bp. For the ApaLI digestion (FIG. 3B), a normal dog (GG) shows products of 397 bp and 115 bp, an affected dog (AA) shows a product of 512 bp, and a carrier dog, (AG) shows products of 512 bp, 397 bp and 115 bp. Thus, this method can be used for identification of normal dogs (i.e., in which both alleles of the F04 gene have G as the nucleotide at a position corresponding to nucleotide position 1298 of SEQ ID NO:1), carrier dogs (i.e., in which one allele has G and the other allele has A as the nucleotide at a position corresponding to nucleotide position 1298 of SEQ ID NO:1) and affected or predisposed dogs (i.e., dogs in which both alleles of the F04 gene have A as the nucleotide as a position corresponding to nucleotide position 1298 of SEQ ID NO:1).

EXAMPLE 4

To confirm the exclusion of the affected allele from the general dog population, we tested 1,000 animals from 67 breeds not known to have the the prcd form of PRA, to establish the absence of the "A" allele. These dogs were tested by Pyrosequencing (Biotage, Charlottesville, Va.; <http://www.pyrosequencing.com/DynPage.aspx>, Fakhrai-Rad et al., 2002; Ronagi et al., 2002; Shendure et al., May 2004) as follows. The technique is based on the amplification of the target sequence with an unlabeled forward primer and a biotin labeled (5' Bio) reverse primer, which are used to isolate a single stranded DNA product. A sequencing primer is used to start a subsequent nucleotide specific primer extension and presence or absence of a nucleotide is recorded in an allele frequency dependent manner based on a luciferase reaction.

```
                                        SEQ ID NO:23
Forward primer:    5'TTGTGAGAGCCGGCAGG3' -

SEQ ID NO:24
Reverse primer:    5'Bio/ATGGCCAAGGTGCTGAGTAG3' -

SEQ ID NO:25
Sequencing primer:5'GGGGCAGCTGAGCCA3' -
```

Figure 4:
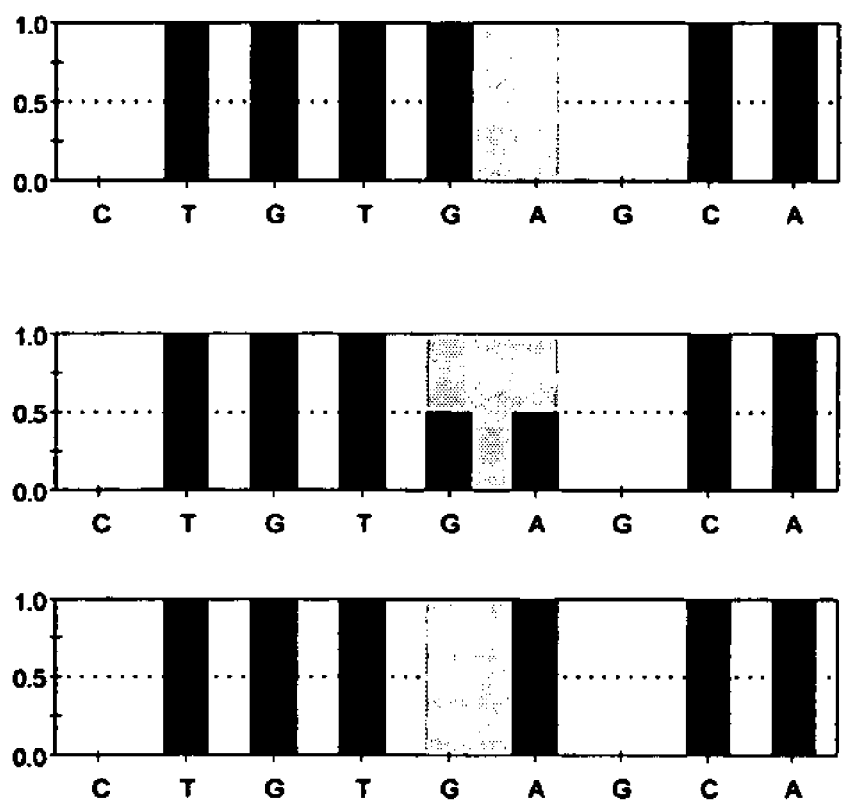
FIG. 4 is an illustration of the experimental setup used to identify whether a dog is a carrier, is affected with or is normal with respect to the prcd mutation, using Pyrosequencing™.

Product: 113 bp (primer sequence is shown in capital letter, the G/A polymorphism is bolded, and Bio indicates the biotin label:

TTGTGAGAGCCGGCAGGggccattttg-gccttctcctgcagactctgtccgggagggatGGGGCA GCTGAGC-CAtgtg/acaccaccctcttcCTACTCAGCACCTTGGCCAT—Bio—SEQ ID NO:26 FIG. 4 illustrates the test set-up for the procedures of this example. Based on the test sequence, a series of nucleotides is injected one at the time during the primer extension (the sequence is shown on the bottom of each panel) and the resulting light reaction is registered (indicated by the bar for each nucleotide, directly proportional to the amount of alleles present). Nucleotides one (C) and 7 (G) of the sequence are negative controls and should not produce any light reaction. Positions 2, 3, 4, 8 and 9 are positive controls and react the same in all samples based on the tested sequence. The mutation in question corresponds to nucleotides 5 and 6. In normal animals, only the G allele is present and produces a reaction of the same strength as the positive controls. In affected individuals the same is true for the A allele, while carriers have both alleles at a 50/50 ratio and, therefore, produce half the intensity at each position. In all cases, the animals tested by Pyrosequencing™ were "GG", i.e., they had G in both alleles of the F04 gene at a position corresponding to position 1298 of SEQ ID NO:1.

It will be appreciated by those skilled in the art that routine modifications can be made to the various embodiments described above. Such modifications are intended to be within the scope of the present invention.

REFERENCES

1. Aguirre, G. D.: Inherited Retinal Degenerations in the Dog Trans. Amer. Acad. Ophth. and Otol. 81: 667, 1976.
2. Aguirre G D, Acland G M. Variation in Retinal Degeneration Phenotype Inherited at the prcd Locus. Exp. Eye Res. 46: 663, 1988
3. Acland G, Fletcher R T, Gentleman S, Chader, G. and Aguirre, G: Non-allelism of Three Genes (rcd1, rcd2 and erd) for Early-Onset Hereditary Retinal Degeneration. Exp. Eye Res.49: 983, 1989.
4 Aguirre, G. and Acland, G.: Inherited Retinal Degeneration in the Labrador Retriever Dog. A New Animal Model of RP? Invest. Ophthalmol. Vis Sci.(Supp). 32(4), 1991;
5. Acland, G., Ray, K., Mellersh, C., Gu, W., Langston, A., Rine, J., Ostrander, E., and Aguirre, G. Linkage analysis and comparative mapping of canine progressive rod-cone degeneration (prcd) establishes potential locus homology with retinitis pigmentosa (RP17) in humans. Proc. Natl. Acad. Sci. USA. 95:3048-3053, 1998.
6. Fakhrai-Rad, H., Pourmand, N., Ronaghi, M. Pyrosequencing: An accurate detection platform for single nucleotide polymorphisms. Human Mutation, 2002; 19(5).
7. Kijas, J. W., Cideciyan, A. V., Aleman, T. S., Pianta, M. J., Pearce-Kelling, S. E., Miller, B. J., Jacobson, S, G., Aguirre, G. D., and Acland, G. M. Naturally-occurring rhodopsin mutation in the dog causes retinal dysfunction and degeneration mimicking human dominant retinitis pigmentosa Proc. Natl. Acad. Sciences USA 99:6328-6333, 2002.
8. Li, R., Mignot, E., Faraco, J., Kadotani, H., Cantanese, J., Zhao, B., Lin, X., Hinton, L., Ostrander, E. A., Patterson, D. F., et al. 1999. Construction and characterization of an eightfold redundant dog genomic bacterial artificial chromosome library. Genomics 58: 9-17.
9. Pearce-Kelling, S. E., Nickle, A., Kijas, J. W., Sidjanin, D. J., Miller, B. J., Aguirre, G. D. and Acland, G. M. 2002.
10. Ronagi M, Elahi E. Discovery of Single Nucleotide Polymorphisms and mutations by Pyrosequencing. Comp Funct Gemon. 2002; 3: 51-56.
11. Shendure J, Mitra R D, Varma C, Church G M. Advanced sequencing technologies: methods and goals. Nature Reviews Genetics, May 2004; 5(5), 335-344.
12. Sidjanin, D. J., Miller, B., Kijas, J. K., McElwee, J., Pillardy, J., Malek, J., Pai, G., Feldblyum, T., Fraser, C., Acland, G. and Aguirre, G. Radiation Hybrid Map, Physical Map and Low-Pass Genomic Sequence of the Canine prcd Region on CFA9, and Comparative Mapping with the Syntenic Region on Human Chromosome 17. Genomics 81:138-148, 2003.
13. Zhang, Q., Acland, G. M., Wu, W.X., Johnson, J. L. Pearce-Kelling, S., Tulloch, B., Vervoort, R., Wright, A. F., Aguirre, G. D. Different RPGR exon ORF15 Mutations in Canids Provide Insights into Photoreceptor Cell Degeneration Hum. Molec. Genet. 11:993-1003, 2002.

The invention claimed is:

1. A method for identifying a dog as genetically normal, as a carrier of, or as predisposed to progressive rod cone degeneration comprising:
 a) obtaining a biological sample comprising nucleic acids from the dog; and
 b) testing the biological sample comprising nucleic acids for a G to A transversion in the F04 gene at nucleotide position 1298 of SEQ ID NO:1, wherein the G to A transversion in one allele is indicative of a carrier of progressive rod-cone degeneration, the G to A transversion in both alleles is indicative of a dog affected with or predisposed to progressive rod-cone degeneration, and the absence of the G to A transversion is indicative of a genetically normal dog.

2. The method of claim 1, wherein the testing is carried out by amplifying the nucleic acids from the biological sample, digesting the amplified nucleic acids with one or more restriction endonucleases and identifying the G to A transversion in the amplified and digested nucleic acids.

3. The method of claim 2, wherein the amplification is carried out by polymerase chain reaction.

4. The method of claim 2, wherein the restriction endonuclease is RsaI.

5. The method of claim 2, wherein the restriction endonuclease is ApaLI.

6. The method of claim 3, wherein the nucleic acids are amplified by using primers of SEQ ID NO:27 and SEQ ID NO:28.

7. The method of claim 1, wherein the testing is carried out by pyrosequencing.

8. The method of claim 7, wherein pyrosequencing is carried out using primers of SEQ ID NOs. 23, 24 and 25.

9. The method of claim 1, wherein the nucleic acid is DNA.

10. The method of claim 1, wherein the nucleic acid is mRNA.

11. The method of claim 1, wherein the biological sample is any tissue containing genomic DNA or mRNA.

12. The method of claim 11, wherein the biological sample is selected from the group consisting of blood, hair, mucosal scrapings, semen, tissue biopsy and saliva.

13. The method of claim 12, wherein the biological sample is blood.

14. The method of claim 1, wherein the dog is selected from the group consisting of akita, American cocker spaniel, American eskimos, Australian cattle dog, Australian stumpy tailed cattle dog, basenji, Bernese mountain dog, border collie, Chesapeake bay retriever, Chinese crested, English cocker spaniel, English mastiff, English springer spaniel, Entlebucher mountain dog, Finnish lapphund, German shorthaired pointer, giant schnauzer, Havanese, Labrador retrievers, lowchen, miniature poodle, miniature schnauzer, Nova scotia duck tolling retriever, Portuguese water dogs, samoyed, silky terrier, spitz, standard poodle, standard wirehaired dachshund, Tibetan terriers and toy poodle.

* * * * *

SEQUENCE LISTING

<160> NUMBER OF SEQ ID NOS: 34

<210> SEQ ID NO 1
<211> LENGTH: 18592

<212> TYPE: DNA
<213> ORGANISM: canis familiaris

<400> SEQUENCE: 1

| | | | | |
|---|---|---|---|---|
| cggccaggtg | gcacctctga | ctcccagccc | aaacctgatg | ccagtgtcca | 50 |
| cttctccctg | tcgctccctc | gcgaccccgc | ccttctcaag | acttggtgtc | 100 |
| cctctgcaag | tgtgagaaga | ggtcggctca | cctcttccgc | tttggcttat | 150 |
| gtatttaaa | aatcgttttt | caaagtagag | agcccaggtg | cagccccagc | 200 |
| tctggccctc | cctgggagcc | tgggcaggag | acccctcgac | accgcttcca | 250 |
| tctccttgga | gggaaggaaa | atctagtgca | gaccyctggg | gttttggag | 300 |
| agggctggag | gaagctggat | gctcagaccc | ctgtgtgctc | cacatgctgc | 350 |
| ctgggccacc | tcactgaacc | cctctgacag | gacacccgat | gcctgtgcgg | 400 |
| tgcccttcca | agtggctgct | cagaagcttt | gcactgggaa | agcaagtatt | 450 |
| cgctatttct | atttagtatt | tctatttagc | tttatctcat | cttttacaag | 500 |
| tcttatgtgt | gtttattatg | caggactgta | ttcgcacaga | tgtggaagat | 550 |
| ctaatgtatg | agcagatgca | tatacttatt | tcatgagtgc | acacttaaat | 600 |
| ccagtctttt | atggaagggg | ctatggaaat | cagtaacatt | tggggaggac | 650 |
| tgtccagagg | ggagaacaca | actgctcagc | cgcccctcca | ctccccggcc | 700 |
| tcccttgtct | ttctggcttc | attatctaat | attcttcctc | ccctccccat | 750 |
| ggctctccat | gacatcattg | ttctgccaac | actcaacttc | cagttgctgg | 800 |
| aacatgctct | gtgcttttgt | gtcagccgcc | ccggaagagt | cttctgttgg | 850 |
| sgggaggta | accttccttg | aacacctgca | aattccaatg | ccccagctc | 900 |
| ctctcccaag | cattccctga | cacatgcaac | tccgaaagtg | ctctgcgggt | 950 |
| gcctctcatc | acccaagtcg | ctctactgtg | gtcattaatg | tgacttgcya | 1000 |
| gctcaagtgt | ctagactaga | agcccttga | gggttaggcc | caggtcctag | 1050 |
| tcacatctgt | atccagaatg | gacagcttga | tttaccctgc | caccgcaggc | 1100 |
| gacaacttgg | gcccagtgag | gttaatcagt | ctgcacaagg | tcgggttggc | 1150 |
| tgaccccact | aatcagcttg | agcctcctaa | tccagtggca | gcaggaacct | 1200 |
| caggatgggc | agcagtggct | tgtgagagcc | ggcagggcca | ttttggcctt | 1250 |
| tctcctgcag | actctgtccg | ggaggggatg | ggcagctga | gccatgtrca | 1300 |
| ccaccctctt | cctactcagc | accttggcca | tgctctggcg | ccgccggttc | 1350 |
| gccaaccggg | tccaaccgtg | agaagctgat | ggggccatgg | gcagggatgg | 1400 |
| ggagagagga | gaagctaggg | ggtgaggggt | ggtgcagggg | ctgcctggac | 1450 |
| ctcctgggag | gctggagggc | ggggaggatt | tgcaggagg | tccagagagg | 1500 |
| tttcccatca | gagcacgcgg | gggcgggggc | tcgcaggtgc | tccgagactg | 1550 |
| gctggagtcc | ccgtcccccc | agcccaacac | ggccaggaga | gggggttctg | 1600 |
| ggcccgggcg | ctgcccacag | ctcttccagc | ctcttcctcc | cgcccacagg | 1650 |
| gagcccagcg | gagcagacgg | ggcagtcgtg | ggcagcaggt | cggagagaga | 1700 |
| cctccagtcc | tcgggcaggt | aaggcagagt | ctgggctggg | ggaggcaggg | 1750 |
| tgcgtcgagg | aagcggctgc | cctggccgcc | ccgaccgtgc | ctgggcaggt | 1800 |
| acatgagtgc | acccgagccg | gcgcgccggg | gccccctcgcc | ccagccaccc | 1850 |

-continued

| | |
|---|---|
| ggtccccgtg tgcccggtgg gcagcctcgg tgtctgtgct ccccgcggc | 1900 |
| actgggcgcc csggcctgtc ctctgcaccg cagctgctct gctttgcccg | 1950 |
| agtgcgggt ggtccccgg gtcccatcgg aaggcgcggg gggaccggag | 2000 |
| aggatgggc aggagcagct ccgggcggcc ggctcgctgc ccttcccct | 2050 |
| ccccgcggcc cccgctccgc ctcagccgct ccctgcccc ggccgccggc | 2100 |
| gggattcgcc caccggcccc caataggagg cgcaggagcg gcatgacgtc | 2150 |
| atcggcaccg cctgccattg gctgggcagc tcctgcgggc aggtcgctgt | 2200 |
| ctccagcggc cgaaagttaa ctcttcccta ggccgaagcc atgtggctcc | 2250 |
| acaaggggg aagtttgggg aacttctgga ttcttccttc cctgggtgac | 2300 |
| cagtgtcctt tgatgttagg ggctcctatg cccaacaaac cacggaaaaa | 2350 |
| tcaacatgca tttattaaga acataccgtt gtgcgtgttc ttttgtgccc | 2400 |
| ccggacccac ctrgtggggg agtcctgtgt gaagggacat tctctcctgc | 2450 |
| aaaaggtcta ctagccttct ctcaactcta gtgagacaaa gcacatgatg | 2500 |
| cccttgggct ccggggcctg tggctggagg gagtctcccc acagcgctca | 2550 |
| gatggctgag ccagtgagcg tgcctgcctg ctggggcacy ccaccggctc | 2600 |
| tcctccrggt gtgtaggacc tgcctgggtg cccctcagcc atgtggagac | 2650 |
| tggcgagcca tgagaaatga gaatgggaat ctgtctccgt atgcggcccc | 2700 |
| aaattcctcy tcggtgctgg gattcctcca agctctgaat rtcaggaggg | 2750 |
| cagccctggg catgtgccyg agacaggtat ttctgggcca cccttccttg | 2800 |
| acaatctagg ctagctgaga tggtcatgat actacccaag taggcctgct | 2850 |
| ggtgaaatgg gctgacaaag gtgaaatgat gagcactggg cctcacgcag | 2900 |
| agcaggccct tgaatgacta gtcctccctg ttgagtttgg gtctggaggc | 2950 |
| ggacagccag agtccacatc ctgactccct gcttcctgac cgagagcctc | 3000 |
| tgggaaagct atgtgatctt tctatttgta tataaactgg gattaataac | 3050 |
| agaatggtgt gggggtgttt gtgaggttca aattgagatc atcctaaagc | 3100 |
| acttggcacg aaacagctrt ttaataaatg ccggctagct attctcctgt | 3150 |
| tgttacctgg ctcttgatca gtgttctatt cttcccttga ggtctcttaa | 3200 |
| acgttaactc acttggaagt tgtaacagcc ccagagggtt ggcaagacaa | 3250 |
| gtgtttctat ctccttgttaa tggtggagga aactgaggga aggggaggcg | 3300 |
| tcagtttttc actcgaggtc atccatccta tttgtggctg atggcaactg | 3350 |
| acttcaggta gtcggtctcc tctacatgaa atgggcctgg accctccctg | 3400 |
| tcaggagaaa aaagctgaat ctggaccatc tggcccagcc tcgtgggtc | 3450 |
| tagccagaag gaagcagttg cctgttaact cccagggacc cagttaactg | 3500 |
| gaaaaatcag cctaacatcc aacacctcct gcttcgggtg gctgttgtga | 3550 |
| agggctggtc tggggagcag taggcatgac atttctgctc tgcaattcca | 3600 |
| cagtcacaaa ttccagctga tttcctggct gctcctaccc ctcagtagtg | 3650 |
| gggtgcctcc ctaggcgtgg ggcaaaggga agaagtctgg aaagacggga | 3700 |
| aggacgtccc cttcaatcct ctgactccca tgcttttctg tttagaaagg | 3750 |
| aagagcctct gaagtaagtc ttcacccggt caggcggagc tcggccccag | 3800 |
| ggaytgggat cagctggcag aggcaggtag ggcagggctg caagccttgg | 3850 |

```
aaggtagagg gctgggctgg ggacaaggca ggctctgcaa ggcctggcca         3900
tgagggagca gagctccatg gagggtacac agaaggcggg tggcctctca         3950
tcagctcctg cctcaagcct sctgtggtcc aggccatggc gcaaggcttt         4000
gttagtttta agggaagggc gtgtggtgaa gtggtggtca tgctggcact         4050
gtagtgccag aggacttcta agggagaggg tgtgctctgg aatatccatt         4100
ctgcaatgca agcccctgcc ttgggatggg aggaagtgcc aatctggttt         4150
tctatttcag ttcaagtccc ggctggcctc ttacccacaa agcatgctgt         4200
ggtggaagca gcagcagcag caagaagaaa aatgggaaaa agcagtcatc         4250
aagaaggtag actcctccct ttgagtccct ggacctgcct ggcctccctt         4300
tgccccagac cctggtggtg gggctcctga agcaaggcct ggctggggca         4350
ggctggaggg caaagacgct cattgccctg gcttgggctc ccttcctctg         4400
agatcctgag gatagtctga ggcaggccca gagagggact caggtttctt         4450
atggaaggrc ttctcattca tccctaatat aatccttgca atgacccaag         4500
aagactgggc gtgttattat ccacactttt ggaaatgagg aaacagagag         4550
aggttaagga atctgtccag tgtcatccag ctagttaatc ctgcccccca         4600
cccccaccca cccccgccc tcccagcctc ctttggaggc tgcagagccc         4650
acactcttac ccaccagggc acaggcctct ctgaaatcac ctggaagttt         4700
gcagcttgca gctgctatgt gagagcaggg gttccacggg cccggcagcc         4750
ccaaagcctg tggtccaagg ctgtgtggta tcagtttgcc atggtggcgc         4800
tctagttcc agggcacttg cctctccccg gtccccagag ctcaccccgt         4850
caccagccac tctgctgcag ttctcaataa gaaatgccag ctgggatctg         4900
tgacatgtct gcctgcggct ggaaggaagc atctctcaac ctgtcctctg         4950
agcgtgtctg cgtgcctgtg tgcatgcgtg cgtgtgttcc aaaggggcag         5000
tcgcatgtgg gaagggaaga agcctgacac ttgttcttgt caatctgctg         5050
actgctcagt accacggcgg ctctgccatt tctccctcac agtcctgctc         5100
gacccagagc agagatcaaa gcagatttcc gcttctgctc cctgagatcc         5150
aggcgcagac ctgcaggcag ctgctcccca ctgtctggaa gccattcatc         5200
atgcaaagcg cctcccccacc aaaccctgc ctgcacgtgc atcrtccccc         5250
caccatcacc atccagcccc cagggtgggc agggaggtcc ctgcctagct         5300
gcacaccccc caggccatca agaggcagga gatggggagt tctctcgaca         5350
gcagcctgtc tgccgccctg actccacatc tgagggaagg aaggaaaggg         5400
tgagatgcca cagacagagg ggaccacgct gaagccatgg gggagggct         5450
gctgatcttg ccctggaagc tctagaagt agggcagggt ggaggcaggg         5500
gaagggtcaa accaggggaa ggagctgtgc gctggaatgg cgacagagcc         5550
ccaccgccca ctcgacatgg gccaggagtt cgtgaccacc tgtctcagct         5600
cctgtcagcc tgtctttctc ctgcgaggtg ttggccttcc ttggtgacag         5650
ggctgtcggg ctgagggcca ggggcaccgt tcctggggcc cccatctkcg         5700
tccccgagcc cacctgtgta ttcatccctct aatctgtttg ccatgctcct         5750
gtcacttcag cctcggctct gctctctacc atttccacgt tgcctgcctc         5800
```

| | |
|---|---|
| cttgcactag tctgaggaat tgtcaggcca aggtcacctg gctggacagg | 5850 |
| ggctggccca cggcccagac acacctccac gaggcgacac cccttcgctg | 5900 |
| cactgttcta gggacctgct caggagaggg tggctcctct gggcctcggt | 5950 |
| cccagaggga aggagagaag gggaagggaa gggctgctgg cgatggggggg | 6000 |
| actgtgtcgg ctggccttgg cggttgcccg ggccctggca gctggggtgc | 6050 |
| catgtgggct gggcgggagg ggccctctcc cccagggagc aggctggctt | 6100 |
| cggtgggagc agattgtgtt tacaccttcc ccacacaccc agcccacgct | 6150 |
| cgcctcttat tccccgggac tctcccaccc ctgggctctc tctgcaccac | 6200 |
| gggcacgttt gcagctcctc tcctgctgca ggaagttgcc gccctcagca | 6250 |
| gagmgctcct ctacagaagg ctgccagggc ccaggcgctc cctcctcggc | 6300 |
| ccactatctc ccgtcgtggg gggggaccca gtgtccccaa gaggctgaat | 6350 |
| ccacccaccc cccatttcct tggaaaacag ctgctgcttg ggaatggggg | 6400 |
| caggaaggaa agcccggggg gcttggcaga cttgaccata ataggaggga | 6450 |
| agggattaag ggcaaccaga gagagagggc cgagagagcc ggggcgcctc | 6500 |
| tggcctcagg gtgcatgaga taatgtagaa tttaagctcg gggagtccag | 6550 |
| ctccaagctc tggatttgaa tcttgactcc accatcactt tccagttctg | 6600 |
| tggcctcggg tgggttactg aatgtaaacc tgtctcagag ttgtaagggt | 6650 |
| taaattagat aatgggtata aagtgcttcg cgcacttagt aagcacgcag | 6700 |
| tatatctgag cccagggtgg ggggacagtg tttgtgagct gtcagccact | 6750 |
| gaacaactgg tcactttgca acaaccgtag gttcagaaca gctagtcctt | 6800 |
| tacctcctca ccccatggcc cttcctgccc tgtctttcca catacacaac | 6850 |
| agcagggtga tgggcagttc tggaacaaac cagagcccag cacaggggca | 6900 |
| cctggtagga cccagcaccc gggaaggctg gacgatggag caccacggtt | 6950 |
| gcytctgggt gcctggaacc ctgtccccac ctccagtggg agtcctgacc | 7000 |
| tggacatctt ccctccaact ggctctgcgw ccccaaatga atctcagctc | 7050 |
| ctagagaaga caggaggcca tggccctggt gcctttatgg tcctctgtct | 7100 |
| gaatgctaat ctctttactg gctggagcct gagtgacagg gaaaaggcgg | 7150 |
| ttctgagctg cagggtggcc gagggcggca ggmgggagca gggaggtgct | 7200 |
| gttgtctgct acttctgtgg ctgctgccag tctctcctrg agatgggaac | 7250 |
| atgaccagag agctaatgag gtggcggggg tgggggtggg ggagaaaggg | 7300 |
| aggcagacgg agcagctgca gcagctgcca ctgccctgtg tcaccccagg | 7350 |
| gtgcaaatgc caccacgggg agcaccccgc ccatcccgaa ctgtgtggct | 7400 |
| gtgcagatgc gggcaggatg gtcctgggca caggccttgg tccaagacca | 7450 |
| ggcaggcgtg gtacttgatc tgaggtgggc atcatggcac aggagctggt | 7500 |
| cccaggggtg cccggggacc tttatagaac ctcagtcggg aagaagccca | 7550 |
| agaccttgag ccagagggaa gtaatgcttc tttgtgagcc tcaaaaggag | 7600 |
| ggaaatggcc aaggtttaca gtaatataat gacactaata ttattattaa | 7650 |
| taatggctaa tgtgtctcaa acgcttctta cgtgctaggc gctgtgccaa | 7700 |
| gtgctttatt tatatgcatt gtctcattta tggggcagga actgttgtca | 7750 |
| gtctcatttta cccaataagg aaagtgcttg ctcaaggtca cccacagtga | 7800 |

```
gtagtgaagc caggacgtgt tccccggcaa ggtgatgtaa aagcctgtga    7850
aggtrttggg cctcgaggac atcctgggag tgtgacctgt ccaccagggc    7900
acagggcatg agagctggca accctccctg gtgatactgc cgctgctcag    7950
tctgcagaaa ctcatcattc caggctggac cagactctgg gccccgaggg    8000
cagtgaccag agccaccttt ccaggatctg tcatgctcct cagggaggaa    8050
gcagtggcca ctggcaggga tgacagatat caaggttgtc actcattgct    8100
gctgttgctc tgctgtttcc tccaaccagg ggcagagccc tgggggtaag    8150
ggagggtggc agccagcagc ccagccagag aaggaggagc cagaggagga    8200
aggctttgtt gtttgttttt acaggggggay ggtgcagggc tttaaggagg    8250
tggcttcaag acctgctgac tttagccata aactggtacc taagggtgct    8300
ggaccctctc tgtgggatac atatgccccc tagtggggat taagcctgga    8350
gggtggctga gaaaattaaa gcaaaacaaa acaaaaaaag atttactgat    8400
aggctatatg acctccgaac ctggatagga agggccaggg ctggcccccct   8450
gtgtccccga gattgcacaa gcacgcacag gtttaagaca atttgcagaa    8500
cccaggtgaa cgaagcattg aaagaaatta tttaatttat tccttggtca    8550
tttatttaag aagcatgtat cgggagcctg tgatgtacac accctgtggt    8600
aggtgttgga gtcagacagc aatcaaaggg acggcgcccg atgtgccaat    8650
gaggacgaca gaaagatcct ggccgaggag gccagttgtg caagctcagc    8700
cgctgcctgc cacgactttt acttctctgg acctcagtct ccccatgtaa    8750
taggcagtgt tgaacctaag tgggctggtg cagaggatgg gaaggaccac    8800
tgactaccct ggtaaaatga aggggatgga cttcttgacc tcggggggggg   8850
cccttccaga ttcaagacag gctacagtgg acagtgtttg gaggtgctga    8900
caacggtgac tcgcccactc agcaagcgtg tatggagctc ctgtatgcca    8950
ggcattgtgg gtgcagaaaa tgaagcrccc agaaaactgg acaaaactga    9000
agaagcaaca gacacttgac tacaaggaac atccaagatg gtgatcccgt    9050
gaccacctca gcatctacct cccacaggtc cctgcctgag cacagggagg    9100
ggaaacccag aggactgcag tggtcttgtt cagctgagga gacaagatca    9150
gagctcagaa cagtgtgctg ttcctaaaga tatacacaca catcaatggc    9200
atctccaaaa cagacacaac gaagatgatc caatggagaa agaaaagccc    9250
ttttgaggaa acacaaaaag tgctaaccat aaaagaaaaa aacagataaa    9300
ttggacttga tcaaaattct tggaaagact ggaagagaat actagccaag    9350
caaaaatccg aacaagggcc tgtatccaaa atatataaag aactttaca    9400
actcaataag aagacgacag cccaacggaa aagtggggga gggttttaat    9450
agacacttcg caagaaacta gacatatggc caataaacac ataaaaagat    9500
acacaacatc ctaagccatc aaggaaatgc aaattaaaac cacaatgaga    9550
tactactgca cactcaccag aatggataaa agatggacca taatagacgt    9600
gggtgaaggt gtggagcaac ttgtaaccct gtcatacgtt gctgggaaac    9650
ctgtttggca gtttcttagg atgtaatcca agaggagtga acatgtaggt    9700
ccacacaaag atttgtacag agatgttcac agcagtgtta ttatcaataa    9750
```

| | |
|---|---|
| ttagtatcca aactggaaac aacgcagata gccatcaaga ggtaaatgga | 9800 |
| taaaaaaaaa aaaaaaaaaa aggaggcggt gtattcatac aatggaatac | 9850 |
| gattcagcaa taaaaaggca ttgagctact atgtgagcca taacacaggg | 9900 |
| caatgagaga agccagatgc taaagagcac ctacagtatg aatccattta | 9950 |
| taggagattc tagaacaggc aataactaat cgggagtggc agaaagcaga | 10000 |
| tcagtggttg cccgggggcca gggctggata tggacactgt gaaatagcag | 10050 |
| gttggtaccc tccagggggga tggagatgtt ctaaattgag actggggttg | 10100 |
| tggttttatg ggtgtatcac tggctggact attttaaatg gatgcacttt | 10150 |
| gttatatgta aattataccct caataaagat gacttaaaga gttaaaaaaa | 10200 |
| aaaaaaaaa aaagaaccac gagaatgaar acctgatcct tgtcttgctt | 10250 |
| acagtctagt gaaaacgmca gatgtgaaaa caaacaacca taaggcggtg | 10300 |
| agtagcctaa gaagcatgct caaataacaa gagttctgtt tatgaagggc | 10350 |
| tccctcgcgc cagacccaca gaggtggctt ggcgtcactg ttctagaagt | 10400 |
| ccagataaga aaagaggctg agatggaggg gaagttgttc acgcaggatt | 10450 |
| actcagctag aatcagcagg cctgggactg ggctccaagg ctgcctgggt | 10500 |
| tcagagcagg tgccacagca gcctgtggca ggacaccgag cagagagctc | 10550 |
| gggactgttg cagcttctca ggtgagactt tgcggaggag gtattgacac | 10600 |
| aggagttgga atttgctcag cagagtagag gatgcgggga aggaaatttc | 10650 |
| aaagcaaagg gaacaaacaa tatgagcaaa ggctgggcaa cacttgtgag | 10700 |
| aaggcagggt tcctgggaat ggagagacgt gtcccgaaaa gagcagaaga | 10750 |
| ggtcaacagg atattacatg ttcttcgcat tcacttattt ttttaagaac | 10800 |
| ctattaagca ataatttta cgagaggcaa cagctctgca gggcaggcaa | 10850 |
| gtgawgtatg tgctcttggc aaacgcaggg aagaacccac cgtgatgcca | 10900 |
| aggttgcctc tttagggaaa gggggttctcc ctgtgacatt tctcctcctc | 10950 |
| caggaggtta aggctgtgtt ccaggatccc aggtttctgc tgaacaccct | 11000 |
| ttgtggcact ctttcacggt cctgagaaat cccaggagga aaaaaaaaaa | 11050 |
| aacaaaaacc cgcctgtgct tttatgctgg gctttctggc tggaggaagt | 11100 |
| caagtcactg gagcgaagca aaatgtgtca cactgtcatg gtgcgttctt | 11150 |
| ctggaaactc agcacagcag tgaggtttgg aggctttgag gctggactgg | 11200 |
| ctgaggtcag atctcagcgc tcttcacac tgattacttt cccctttctg | 11250 |
| cactttggct tctttagaag attgcaaaag aggggtgatc ataagagggc | 11300 |
| agatgtgaga atgaagggac agtacgtgca atgtgctcag tcagactcat | 11350 |
| cgagtctgag acgttaattt agcctgtata gccttttgta tgacagtcag | 11400 |
| tcctccataa atcagttttt taaaagaag gtgcttagag cagagcctgg | 11450 |
| cccagagcaa acatttaata gacagtagct tttgtgtttt caaaaaggtg | 11500 |
| acatgcacat gtcatcccctt ttattttgct gtgacccgtt ctttcagaga | 11550 |
| attataatga agcgggattt gggacatgtt gatcatatca tttaggatga | 11600 |
| ttgtgactct taacagaaca cccaacttag ggtggctcaa acaggaagga | 11650 |
| gatttctaaa tctcacattc tggggcgcct gggtggcaca gttggttaaa | 11700 |
| cattcgactc ttggttttgg ctcaggtcat gatctcaggg ttgtgagatg | 11750 |

| | |
|---|---|
| gggccctgtg ttggagtctg cgctcagctc acaattctct ctctcctcca | 11800 |
| cttctgcccc tcctgccctc tctaaaataa acatttgagg gttttttttaa | 11850 |
| aaagatttta tttagttagt tgagagagag acagacagag acagagagac | 11900 |
| agagagtgag catgtgtgag cacaggtggg aagggcaga gggagcagca | 11950 |
| gaatccctgc tgagcaggaa gcccaacaca gggcttgatc ccaggaccaa | 12000 |
| gatcaagacc cgagccaaag gcagatgctc atccaactga gccagccagg | 12050 |
| caaccctaaa ataaatgtct ttttttaaaa aatcatcctg tgtttcactg | 12100 |
| aaactaacat gccattgctt gtgagatgcc ccttgcattc agaaatatta | 12150 |
| aaatataaaa atgtgtgtct ttgarttgaa acaaaaggtc tgaaggtagg | 12200 |
| gggctctagg actggtaatt tggcagttca ccatgaggac tctttgtcct | 12250 |
| ttgtttccac tctgccatcg tcagacctta ggctctggct ttgaggcaag | 12300 |
| cctcatggat gcaagatggc tgccagggcc tcaagcatca agtcttcaga | 12350 |
| gcctcccaaa gccagaagag aggctgctgt ttttaaaaac aagaaaaact | 12400 |
| ttcccaaact ttgcttaatt gcatcacaaa ccctttttctg aattcctggc | 12450 |
| agaaggaata gatttatcat aagggtctgg tgccgactct tcaagattcg | 12500 |
| cccttagggc cggggaggag cttgcctcca ctgaagcacc gagctccagt | 12550 |
| tctgttgtga gatggaggaa gaacagctgt gagctggcaa tgagcagcgc | 12600 |
| tgccatacag atraaccgcc tgtgaatcac cggtcaactg tgcccgacag | 12650 |
| aagcagctga ctgcttggga tattcctacc caccttcctg ttcctatcaa | 12700 |
| caatggtaga gcttcctctc caggttaaga aattaacctc catattccaa | 12750 |
| agacttggtt tcctattaat gtggcttttcg ggtaccgtat ccaaaatcct | 12800 |
| atccggatgg aacccagtga gttagccacc tgagcacagc aggccaatgg | 12850 |
| actagatttc acctccgtgc tcagagccaa ggccccctga ccgcaccgag | 12900 |
| gactgtggcc ttgctcagcc tgggatctac ttctgtcact gaccactaga | 12950 |
| ttgggggact ccgtgtcagt gaatacagat ccatgctagc ctaggatgac | 13000 |
| ggctacgtaa caattccact gcacataaaa actcaagtgt cccagacctc | 13050 |
| ggggcgcctg gctggcttag ggaggactga ctcttaatct cagagtcttg | 13100 |
| agttcaagcc ctgtgttggg tgtggagcct acttaaaaaa aaaaagaaga | 13150 |
| agaagaagaa ggagaaggag aaggagaagg agaaggagaa ggagaaggag | 13200 |
| aaggagaaga agaagaagaa gaagaagaag aagaagaaga agaagaagaa | 13250 |
| gaaagaagaa gaagaagaag aagaagaatt agaaatcaca acattgatgc | 13300 |
| tttgatctcc acagctctga actcccgcct gctccttcag aaatctgatg | 13350 |
| cgttctctgt tgtcttttcca ctgatttttt tcttttttttt ttaagatttt | 13400 |
| atttatttga cacacagaga gatcagcagg gggagcatca gagggagagg | 13450 |
| gagcagcagg ctccccgctg agcaggaagt ccaacatggg gctcaatccc | 13500 |
| aggaccctgg gatcatgacc tcagccaaag gcagatgttt aacccactga | 13550 |
| gccacccagg tggccctgat tttttttta agattattta tttatttttag | 13600 |
| ggatccctgg gtggcgcagc ggtttaccgc ctgcctttgg cccagggcgc | 13650 |
| aatcctggag acctgggatc gagtgccaca tcgggctccc ggtgcatggg | 13700 |

```
gcctgcttct cnctctgcct atgtttctgc ctctctctct ctctctgtgt     13750
gactacaata aattaaaaaa tatttttttaa tattatttat ttattttaaa    13800
atatttattt tatttattca tgagagacac agagagagag gcagagatac    13850
aggcagaggg agaagtaggc tcccacagga cttgatccca ggaccccagg    13900
atcacgacct gaatccaagg cagatgctca accactgagc cacccaggtg    13950
tcccattaaa gattatttat ttgacagaga gagagagagc aggagcagag    14000
gggcacaggg agaagaagac ttcctgctga tcgaggagcc cgacatgggg    14050
cttgaaccta gaaccctaag atcatgaccc aagttgaagg cagatgctta    14100
accaatggag ccaccaggtg ccccatcctc ccctatttct ggactgccca    14150
ggcagtgtgc cctctgcctg ccactcttcc tgcttgtgtg ctctattttt    14200
caaataaata aattaattaa aaaataataa tcttgaggca cctgggtggc    14250
tcagtggttg aacatctgtc tttggctcag ggcgtgatcc tggggtcctg    14300
ggatcgagtc ccacattggg ctccctggat ggagactgct tctctctctg    14350
cctgtgtctc tgcctctctc tctctgtgtg tgtgtgtctc tcatgaataa    14400
ataaataaaa gggatccctg ggtggcacag tggtttagcg cctgcctttg    14450
gcccagggcg cgatcctgga gacctgggat cgaatcccac gtcgggctcc    14500
cggtgcatgg agcctgcttc tccctctgcc tatgtctggg atccctgggt    14550
ggcacagcgg tttggtgcct gcctttgggc cagggcgtga tcctggagac    14600
ccgggatcga atcccacatc gggctcccgg tgcatggagc ctgcttctcc    14650
ttctgcctgt gtctctgcct ctctctctct ctgtgtgact atcatgaata    14700
aataaataaa atcttaaaaa aaaaataaat aaataaaatc ttttttattag   14750
atttttattta aatctttta ttagatttta atctcactgc gttttgctcc    14800
ggcctctcgg cgcctgccca gccacccgag acatgccacc tgcggtgaac    14850
ctgctgctct tctactaggt gtcctgtcag gtgtgaaagc tccactgtag    14900
accgtggcat tgtggctcct ctcaagccca gaagaatgct ccatgctcct    14950
cacacgcact agctggcaac cggtctggga ctcaagacag ccctgctaga    15000
gcccagagcc cccagtcttt gcagccatca gcyrctgcag cctctcctcc    15050
tcactctgct tgccataaag tggctcaaaa ccacggaaca ggtgcccatc    15100
attcccctga gtaatttcat cccaaccacc cctgcaaaca cacaaaaccc    15150
ttctttgctc ctctcccca tgcccaaaag ccctatagta agactgatgt    15200
atagatatac gaagttcagt acatcttagt ggtgagagta tggactctgc    15250
aggctggcct caaaccttga ccccagcaat cactagttgt gtgaatttgg   15300
gaaagtcacc tcatctctca ctcacctcac ctcatctgcg aaatgcrggt    15350
agtgatagwg ccccttcagag ggcagcggtg cacattaaac aaattggtgt   15400
gcgttcagta ctccaggagt ggacggcgca tggtaagtgc taccyggtat    15450
ccactctcgc tgttattcgg cctgcagcgg gtcccttgcc tccatccaag    15500
cagctctggg gaacttccac attcaaaact ccctctccga gtctgaaaat    15550
gaaaggaact tagttttcag ggagagagcc cattcctcct ttccctattc    15600
tacaaaactg tattcaaggg caagacagaa atgcaagggc cagtttcata    15650
agacagatgt tactgccaag tgagtcaatg attatctgtt gtgtacgtgg    15700
```

```
gcagaggcag aggaataaca accagactct gggaggcaat taaaaagaaa        15750
aaaaaaaaaa gtaaaagagt gtctcatgga gcgcctgggt ggctcagtcc        15800
gttaagcctt ggacttttgg tttcccctca ggtcatgatc tcagggtcgt        15850
gggacccagc cctggggcgg gctctgtgat cagtggggag cctgcttgag        15900
attccctcct tctgctgtgc acactctctc tctaaaataa atacgtcttt        15950
agaagagcaa gcgagcgaga gatgcttccc gcctagaaga gcttacaatc        16000
aaatcagggg aggcaaacat aaacaagtgt ggcaacttga taataagcac        16050
ctgcgaccta tggccataca cagaataaca taacccagac taaatgccac        16100
tgcatagtca ctagcgggtt gatgacaacg gggggaggct aatgctgaaa        16150
aggcctttct gtcttataag tttaaactaa tttctggggg cacctgggtg        16200
gctctggttg agcatctgcc tttggtcgt cgtcccaggg tcctgagatc         16250
gagtccctca tccggctccc agccccgtag gagcctgctt ctccctctgc        16300
ctcttcctct ctgtctctca tgaataaata aataaaaatt ttaagggatg        16350
cccgggtggc tcagcggttt agcgcctgcc tttggcccag ggtgtgatcc        16400
tggggtcccg agatcgagtc ccacatcgag tcccacatcg agttccggga        16450
tcgagtccct gcagggaacc tgcttctccc tctccctgtg tgtgtgtctc        16500
tctctctttc tgtatctctc atgaataaat aagaaaatc tttaaaaata         16550 aataaataaa aacagtattt aaaaaaatga actaatttcc aagtaggtgt        16600
aaattctggc tcggactagt gaatggctct ggctctgctg catcacccac        16650
cgccagggct ctgggccgct ccgagccccg ctcgccggcg cccctgccg         16700 cccgggcctc ccgccttcac cccaacccgc agggcggcgg agccctaggc        16750
ccaatcggcc ccgggaacct gccgcctctt ctctagcgca acccagcacc        16800
cagatgaccc cttttccgcc ccaggtgcag tccggccggg ccctggtgtc        16850
ctcacccgtt cccctaggga gacccctctc gaaccttctg cgccacccta        16900
ctctacgcca gggaaaatct gtgcactcag tagataaatg cttgtaactg        16950
aagcaaccgt ctccgtggct ccagaatcgc gctgaggatg ctgctgccgc        17000
accccaccct cccccggctc cggcggaggt tgtttggact acacttccca        17050 tgaggccccct ctcaacatcg cgataactct cgcgagaccg ctgggaagag       17100
ttgtgcgcag gcgcagcccc gccttcttgt cgaggcaggc cgcgtggccg        17150
gcagtcatgg cggctccttg ctggcccgac cgggacaggg agtctggagy        17200
ctctggctgt ggtaaggttg tcgaggcggg cagacgggat cgtccttggc        17250
ccggcgctag ttcgctcggc ctcccttttcc tcggggcgg gatgatgacg        17300 gtaaagccgg tcttcctcgt agggtggttg ggttagttga gatgctggat        17350
cggaaaacgc tttctgagcg gcgcgagtgt tgacgatcga agggagagag        17400
ctcaggcccc ccttggagtc agagggcccc tcctgggggg ggggtcctc         17450 cagcctgtgc agcccgtgt gtgccctgcg ggtctcccgg gccgcccac          17500 gggaggctgc cggtggtagt tcttaatcca catcaagtgt taacgtgagg        17550
gtcctggagt gccccgaggt cggccctggt cagtggttcg tattcagtcc        17600
tacagatagt agtaaagggg cttgtagatt ttggaaagcc ataatgctct        17650
```

-continued

| | |
|---|---|
| gcgccctacc ttccatgttc attttttttc ccctctctct tcccgtacag | 17700 |
| ggttttcttt gcgtcgcaga cctgcaggtt gaagcttaaa agtagcgaat | 17750 |
| ggggagccct gtgaaatggg taaggatggg tgctggcagg gcccgggtgg | 17800 |
| tgaccagaag tgagaaagtc gagatggtgg gcaggcctgc cacacccggc | 17850 |
| cgccgcacgc tttactttac taattttatt ttttttaaa grtttaatta | 17900 |
| attaattaat taatgatagg cagagacaca ggcagaggga gaagcaggct | 17950 |
| ccgtgccggg agcccgacgc gggactccag gatcgcgccc tgggccaaag | 18000 |
| gcaggcgcca aaccgctgag ccacccaggg atcccacttt accgatttta | 18050 |
| agttcggttc ttaggaacac gtggacgcac gcatccggtt agggtgagaa | 18100 |
| gaaaacggac ccgggtcctg gaagcgagca gggccttgcc agtgtgactc | 18150 |
| ggcgccgcta ggtgtcactg tttggattca aaccggttgc cgcgcacgag | 18200 |
| gttggcgggg aggcttagga aatgggcttc ggtggggttt ggaagtattt | 18250 |
| gtggatgatt taaagttatc tttgtcttaa agggctcttt tgtgaagagt | 18300 |
| tttgatgcgt tgaggctcag cttttttttt tttttttttt taaggtttgt | 18350 |
| attcatttt tcacagagag gcagagggag gagaagcttg ctgcctgcag | 18400 |
| agagcaggat gcgagactcg atccctggat ttcgggatca cgcccagagc | 18450 |
| caaaggcaga cacgcaacta ctgagccacc caggcgtccc gaggccccag | 18500 |
| cttcttaaat aaccaatctt gagaataaca tcttgacctc atttctctta | 18550 |
| gaatatactt tgttacattt cccttagaga ttaaaggtgt tg | 18592 |

```
<210> SEQ ID NO 2
<211> LENGTH: 54
<212> TYPE: PRT
<213> ORGANISM: canis familiaris

<400> SEQUENCE: 2

Met Cys Thr Thr Leu Phe Leu Leu Ser Thr Leu Ala
                5                   10

Met Leu Trp Arg Arg Arg Phe Ala Asn Arg Val Gln
        15                  20

Pro Glu Pro Ser Gly Ala Asp Gly Ala Val Val Gly
25                  30                  35

Ser Arg Ser Glu Arg Asp Leu Gln Ser Ser Gly Arg
            40                  45

Lys Glu Glu Pro Leu Lys
    50

<210> SEQ ID NO 3
<211> LENGTH: 695
<212> TYPE: DNA
<213> ORGANISM: canis familiaris

<400> SEQUENCE: 3
```

| | |
|---|---|
| agtggcagca ggaacctcag gatgggcagc agtggcttgt gagagccggc | 50 |
| agggccattt tggcctttct cctgcagact ctgtccggga ggggatgggg | 100 |
| cagctgagcc atgtrcacca ccctcttcct actcagcacc ttggccatgc | 150 |
| tctggcgccg ccggttcgcc aaccgggtcc aaccggagcc cagcggagca | 200 |
| gacggggcag tcgtgggcag caggtcggag agagacctcc agtcctcggg | 250 |

```
cagaaaggaa gagcctctga agtaagtctt cacccggtca ggcggagctc         300
ggccccaggg aytgggatca gctggcagag gcagttcaag tcccggctgg         350
cctcttaccc acaaagcatg ctgtggtgga agcagcagca gcagcaagaa         400
gaaaaatggg aaaaagcagt catcaagaag gtagactcct ccctttgagt         450
ccctggacct gcctggcctc cctttgcccc agacctggt ggtggggctc          500 ctgaagcaag gcctggctgg ggcaggctgg agggcaaaga cgctcattgc         550
cctggcttgg gctcccttcc tctgagatcc tgaggatagt ctgaggcagg         600
cccagagagg gactcaggtt tcttatggaa ggrcttctca ttcatcccta         650
atataatcct tgcaatgacc caaaaaaaaa aaaaaaaaa aaaaa              695
```

```
<210> SEQ ID NO 4
<211> LENGTH: 20
<212> TYPE: DNA
<213> ORGANISM: artificial sequence
<220> FEATURE:
<223> OTHER INFORMATION: RT-PCR forward primer

<400> SEQUENCE: 4
caccttggcc atgctctggc                                          20

<210> SEQ ID NO 5
<211> LENGTH: 25
<212> TYPE: DNA
<213> ORGANISM: artificial sequence
<220> FEATURE:
<223> OTHER INFORMATION: RT-PCR reverse primer

<400> SEQUENCE: 5
aatgcatata aataaagcac ttggc                                    25

<210> SEQ ID NO 6
<211> LENGTH: 18
<212> TYPE: DNA
<213> ORGANISM: artificial sequence
<220> FEATURE:
<223> OTHER INFORMATION: RT-PCR forward primer

<400> SEQUENCE: 6
ccagtggcag caggaacc                                            18

<210> SEQ ID NO 7
<211> LENGTH: 18
<212> TYPE: DNA
<213> ORGANISM: artificial sequence
<220> FEATURE:
<223> OTHER INFORMATION: RT-PCR reverse primer

<400> SEQUENCE: 7
ccaagccagg gcatgagc                                            18

<210> SEQ ID NO 8
<211> LENGTH: 29
<212> TYPE: DNA
<213> ORGANISM: artificial sequence
<220> FEATURE:
<223> OTHER INFORMATION: reverse primer located on exon 1

<400> SEQUENCE: 8
ccaaggtgct gagtaggaag agggtggtg                                29
```

<210> SEQ ID NO 9
<211> LENGTH: 27
<212> TYPE: DNA
<213> ORGANISM: artificial sequence
<220> FEATURE:
<223> OTHER INFORMATION: reverse primer located on exon 3

<400> SEQUENCE: 9
agtccctggg gccgagctcc gcctgac                                    27

<210> SEQ ID NO 10
<211> LENGTH: 29
<212> TYPE: DNA
<213> ORGANISM: artificial sequence
<220> FEATURE:
<223> OTHER INFORMATION: forward primer located on exon 1

<400> SEQUENCE: 10
caccaccctc ttcctactca gcaccttgg                                  29

<210> SEQ ID NO 11
<211> LENGTH: 28
<212> TYPE: DNA
<213> ORGANISM: artificial sequence
<220> FEATURE:
<223> OTHER INFORMATION: forward primer located on exon 3

<400> SEQUENCE: 11
agggactggg atcagctggc agaggcag                                   28

<210> SEQ ID NO 12
<211> LENGTH: 1084
<212> TYPE: DNA
<213> ORGANISM: artificial sequence
<220> FEATURE:
<223> OTHER INFORMATION: EST clone contig

<400> SEQUENCE: 12
gagcagctgc agcagctgcc actgccctgt gtcaccccag ggtgcaaatg          50
ccaccacggg gagcaccccg cccatcccga actgtgtggc tgtgcagatg         100
cgggcaggat ggtcctgggc acaggccttg gtccaagacc aggcaggcgt         150
ggtacttgat ctgaggtggg catcatggca caggagctgg tcccaggggt         200
gcccggggac ctttatagaa cctcagtcgg gaagaagccc aagaccttga         250
gccagaggga agtaatgctt ctttgtgagc ctcaaaagga gggaaatggc         300
caaggtttac agtaatataa tgacactaat attattatta ataatggcta         350
atgtgtctca aacgcttctt acgtgctagg cgctgtgcca agtgctttat         400
ttatatgcat tgtctcattt atggggcagg aactgttgtc agtctcattt         450
acccaataag gaaagtgctt gctcaaggtc acccacagtg agtagtgaag         500
ccaggacgtg ttccccggca aggtgatgta aaagcctgtg aaggtattgg         550
gcctcgagga catcctggga gtgtgacctg tccaccaggg cacagggcat         600
gagagctggc aaccctccct ggtgatactg ccgctgctca gtctgcagaa         650
actcatcatt ccaggctgga ccagactctg ggccccgagg gcagtgacca         700
gagccacctt tccaggatct gtcatgctcc tcagggagga agcagtggcc         750
actggcaggg atgacagata tcaaggttgt cactcattgc tgctgttgct         800
ctgctgtttc ctccaaccag gggcagagcc ctgggggtaa gggagggtgg         850

| cagccagcag cccagccaga gaaggaggag ccagaggagg aaggctttgt | 900 |
| tgtttgtttt tacaggggga cggtgcaggg cttaaggag gtggcttcaa | 950 |
| gacctgctga ctttagccat aaactggtac ctaagggtgc tggaccctct | 1000 |
| ctgtgggata catatgcccc ctagtgggga ttaagcctgg agggtggctg | 1050 |
| agaaattaaa gcaaaaaaaa aaaaaaaaaa aaaa | 1084 |

<210> SEQ ID NO 13
<211> LENGTH: 707
<212> TYPE: DNA
<213> ORGANISM: artificial sequence
<220> FEATURE:
<221> NAME/KEY: unsure
<222> LOCATION: 598, 602
<223> OTHER INFORMATION: Clone 9 sequence; RT-PCR product

<400> SEQUENCE: 13

| caccttggcc atgctctggc gccgccggtt cgccaaccgg gtccaaccgg | 50 |
| agcccagcgg agcagacggg gcagtcgtgg gcagcaggtc ggagagagac | 100 |
| ctccagtcct cgggcagaaa ggaagagcct ctgaagtaag tcttcacccg | 150 |
| gtcaggcgga gctcggcccc agggactggg atcagctggc agaggcagtt | 200 |
| caagtcccgg ctggcctctt acccacaaag catgctgtgg tggaagcagc | 250 |
| agcagcagca agaagaaaaa tgggaaaaag cagtcatcaa gaaggtagac | 300 |
| tcctcccttt gagtccctgg acctgcctgg cctccctttg ccccagaccc | 350 |
| tggtggtggg gctcctgaag caaggcctgg ctggggcagg ctggagggca | 400 |
| aagacgctca ttgccctggc ttgggctccc ttcctctgag atcctgagga | 450 |
| tagtctgagg caggcccaga gagggactca ggtttcttat ggaaggrctt | 500 |
| ctcattcatc cctaatataa tccttgcaat gaccccaaga ccttgagcca | 550 |
| gagggaagta atgcttcttt gtgagcctca aaaggaggga aatggccnag | 600 |
| gnttacagta atataatgac actaatatta ttattaataa tggctaatgt | 650 |
| gtctcaaacg cttcttacgt gctaggcgct gtgccaagtg cttttatttat | 700 |
| atgcatt | 707 |

<210> SEQ ID NO 14
<211> LENGTH: 562
<212> TYPE: DNA
<213> ORGANISM: artificial sequence
<220> FEATURE:
<223> OTHER INFORMATION: RT-PCR exons 1-4

<400> SEQUENCE: 14

| ccagtggcag caggaacctc aggatgggca gcagtggctt gtgagagccg | 50 |
| gcagggccat tttggccttt ctcctgcaga ctctgtccgg gaggggatgg | 100 |
| ggcagctgag ccatgtrcac caccctcttc ctactcagca ccttggccat | 150 |
| gctctggcgc cgccggttcg ccaaccgggt ccaaccggag cccagcggag | 200 |
| cagacgggc agtcgtgggc agcaggtcgg agagagacct ccagtcctcg | 250 |
| ggcagaaagg aagagcctct gaagtaagtc ttcacccgt caggcggagc | 300 |
| tcggccccag ggactgggat cagctggcag aggcagttca agtcccggct | 350 |
| ggcctcttac ccacaaagca tgctgtggtg gaagcagcag cagcagcaag | 400 |
| aagaaaaatg ggaaaaagca gtcatcaaga aggtagactc ctcccttga | 450 |

```
gtccctggac ctgcctggcc tcccttttgcc ccagaccctg gtggtggggc       500
tcctgaagca aggcctggct ggggcaggct ggagggcaaa gacgctcatt       550
gccctggctt gg                                                562

<210> SEQ ID NO 15
<211> LENGTH: 21
<212> TYPE: DNA
<213> ORGANISM: artificial sequence
<220> FEATURE:
<223> OTHER INFORMATION: RT-PCR forward primer from exon 3

<400> SEQUENCE: 15
cagtcgtggg cagcaggtcg g                                      21

<210> SEQ ID NO 16
<211> LENGTH: 25
<212> TYPE: DNA
<213> ORGANISM: artificial sequence
<220> FEATURE:
<223> OTHER INFORMATION: RT-PCR reverse primer from exon 8

<400> SEQUENCE: 16
aatgcatata aataaagcac ttggc                                  25

<210> SEQ ID NO 17
<211> LENGTH: 316
<212> TYPE: DNA
<213> ORGANISM: artificial sequence
<220> FEATURE:
<223> OTHER INFORMATION: RT-PCR product

<400> SEQUENCE: 17
cagtcgtggg cagcaggtcg gagagagacc tccagtcctc gggcagaaag        50
gaagagcctc tgaagtaagt cttcacccgg tcaggcggag ctcggcccca       100
ggggtgcccg gggacctttta tagaacctca gtcgggaaga agcccaagac      150
cttgagccag aggaagtaa tgcttctttg tgagcctcaa aaggagggaa        200
atggccaagg tttacagtaa tataatgaca ctaatattat tattaataat       250
ggctaatgtg tctcaaacgc ttcttacgtg ctaggcgctg tgccaagtgc       300
tttatttata tgcatt                                            316

<210> SEQ ID NO 18
<211> LENGTH: 20
<212> TYPE: DNA
<213> ORGANISM: artificial sequence
<220> FEATURE:
<223> OTHER INFORMATION: RT-PCR forward primer from exon 2

<400> SEQUENCE: 18
gcagcaggtc ggagagagac                                        20

<210> SEQ ID NO 19
<211> LENGTH: 22
<212> TYPE: DNA
<213> ORGANISM: artificial sequence
<220> FEATURE:
<223> OTHER INFORMATION: RT-PCR reverse primer from exon 5

<400> SEQUENCE: 19
cttccctcag atgtggagtc ag                                     22
```

<210> SEQ ID NO 20
<211> LENGTH: 796
<212> TYPE: DNA
<213> ORGANISM: artificial sequence
<220> FEATURE:
<223> OTHER INFORMATION: RT-PCR product no. 1

<400> SEQUENCE: 20

| | | | | | |
|---|---|---|---|---|---|
| gccaccgggt | ccaccggagc | ccagcggagc | agacggggca | gtcgtgggca | 50 |
| gcaggtcgga | gagagacctc | cagtcctcgg | gcagaaagga | agagcctctg | 100 |
| aagtaagtct | tcaccggtc | aggcggagct | cggccccagg | gactgggatc | 150 |
| agctggcaga | ggcagttcaa | gtcccggctg | gcctcttacc | cacaaagcat | 200 |
| gctgtggtgg | aagcagcagc | agcagcaaga | agaaaaatgg | gaaaaagcag | 250 |
| tcatcaagaa | gtttccaggg | cacttgcctc | tccccggtcc | ccagagctca | 300 |
| ccccgtcacc | agccactctg | ctgcagttct | caataagaaa | tgccagctgg | 350 |
| gatctgtgac | atgtctgcct | gcggctggaa | ggaagcatct | ctcaacctgt | 400 |
| cctctgagcg | tgtctgcgtg | cctgtgtgca | tgcgtgcgtg | tgttccaaag | 450 |
| gggcagtcgc | atgtgggaag | ggaagaagcc | tgacacttgt | tcttgtcaat | 500 |
| ctgctgactg | ctcagtacca | cggcggctct | gccatttctc | cctcacagtc | 550 |
| ctgctcgacc | cagagcagag | atcaaagcag | atttccgctt | ctgctccctg | 600 |
| agatccaggc | gcagacctgc | aggcagctgc | tccccactgt | ctggaagcca | 650 |
| ttcatcatgc | aaagcgcctc | cccaccaaac | ccctgcctgc | acgtgcatcg | 700 |
| tccccccacc | atcaccatcc | agccccagg | gtgggcaggg | aggtccctgc | 750 |
| ctagctgcac | accccccagg | ccatcaagag | gcaggagatg | gggagt | 796 |

<210> SEQ ID NO 21
<211> LENGTH: 763
<212> TYPE: DNA
<213> ORGANISM: artificial sequence
<220> FEATURE:
<223> OTHER INFORMATION: RT-PCR product no. 2

<400> SEQUENCE: 21

| | | | | | |
|---|---|---|---|---|---|
| gccaccgggt | ccaccggagc | ccagcggagc | agacggggca | gtcgtgggca | 50 |
| gcaggtcgga | gagagacctc | cagtcctcgg | gcagaaagga | agagcctctg | 100 |
| aagtaagtct | tcaccggtc | aggcggagct | cggccccagg | gactgggatc | 150 |
| agctggcaga | ggcagttcaa | gtcccggctg | gcctcttacc | cacaaagcat | 200 |
| gctgtggtgg | aagcagcagc | agcagcaaga | agaaaaatgg | gaaaaagcag | 250 |
| tcatcaagaa | gagctcaccc | cgtcaccagc | cactctgctg | cagttctcaa | 300 |
| taagaaatgc | cagctgggat | ctgtgacatg | tctgcctgcg | gctggaagga | 350 |
| agcatctctc | aacctgtcct | ctgagcgtgt | ctgcgtgcct | gtgtgcatgc | 400 |
| gtgcgtgtgt | tccaaagggg | cagtcgcatg | tgggaaggga | agaagcctga | 450 |
| cacttgttct | tgtcaatctg | ctgactgctc | agtaccacgg | cggctctgcc | 500 |
| atttctccct | cacagtcctg | ctcgacccag | agcagagatc | aaagcagatt | 550 |
| tccgcttctg | ctccctgaga | tccaggcgca | gacctgcagg | cagctgctcc | 600 |
| ccactgtctg | gaagccattc | atcatgcaaa | gcgcctcccc | accaaacccc | 650 |
| tgcctgcacg | tgcatcgtcc | ccccaccatc | accatccagc | cccagggtg | 700 |

```
ggcagggagg tccctgccta gctgcacacc ccccaggcca tcaagaggca        750
ggagatgggg agt                                                763
```

```
<210> SEQ ID NO 22
<211> LENGTH: 509
<212> TYPE: DNA
<213> ORGANISM: artificial sequence
<220> FEATURE:
<223> OTHER INFORMATION: RT-PCR product no. 3

<400> SEQUENCE: 22
gccaccgggt ccaccggagc ccagcggagc agacgggggca gtcgtgggca        50 gcaggtcgga gagagacctc cagtcctcgg gcagaaagga agagcctctg        100
aagtaagtct tcacccggtc aggcggagct cggccccagg gactgggatc        150
agctggcaga ggcagttcaa gtcccggctg gcctcttacc cacaaagcat        200
gctgtggtgg aagcagcagc agcagcaaga agaaaaatgg gaaaaagcag        250
tcatcaagaa gtcctgctcg acccagagca gagatcaaag cagatttccg        300
cttctgctcc ctgagatcca ggcgcagacc tgcaggcagc tgctccccac        350
tgtctggaag ccattcatca tgcaaagcgc ctccccacca aacccctgcc        400
tgcacgtgca tcgtcccccc accatcacca tccagccccc agggtgggca        450
gggaggtccc tgcctagctg cacaccccccc aggccatcaa gaggcaggag        500
atggggagt                                                    509
```

```
<210> SEQ ID NO 23
<211> LENGTH: 17
<212> TYPE: DNA
<213> ORGANISM: artificial sequence
<220> FEATURE:
<223> OTHER INFORMATION: Pyrosequencing forward primer

<400> SEQUENCE: 23
ttgtgagagc cggcagg                                            17
```

```
<210> SEQ ID NO 24
<211> LENGTH: 20
<212> TYPE: DNA
<213> ORGANISM: artificial sequence
<220> FEATURE:
<223> OTHER INFORMATION: Pyrosequencing biotin labeled reverse primer

<400> SEQUENCE: 24
atggccaagg tgctgagtag                                         20
```

```
<210> SEQ ID NO 25
<211> LENGTH: 15
<212> TYPE: DNA
<213> ORGANISM: artificial sequence
<220> FEATURE:
<223> OTHER INFORMATION: Pyrosequencing oligo probe

<400> SEQUENCE: 25
ggggcagctg agcca                                              15
```

```
<210> SEQ ID NO 26
<211> LENGTH: 113
<212> TYPE: DNA
<213> ORGANISM: artificial sequence
<220> FEATURE:
```

<223> OTHER INFORMATION: Pyrosequencing PCR product

<400> SEQUENCE: 26
ttgtgagagc cggcaggggc cattttggcc tttctcctgc agactctgtc        50
cgggagggga tggggcagct gagccatgtr caccaccctc ttcctactca       100
gcaccttggc cat                                               113

<210> SEQ ID NO 27
<211> LENGTH: 18
<212> TYPE: DNA
<213> ORGANISM: artificial sequence
<220> FEATURE:
<223> OTHER INFORMATION: forward primer

<400> SEQUENCE: 27
ccagtggcag caggaacc                                           18

<210> SEQ ID NO 28
<211> LENGTH: 21
<212> TYPE: DNA
<213> ORGANISM: primer 2
<220> FEATURE:
<223> OTHER INFORMATION: reverse primer

<400> SEQUENCE: 28
ccgacctgct gcccacgact g                                       21

<210> SEQ ID NO 29
<211> LENGTH: 21
<212> TYPE: DNA
<213> ORGANISM: artificial sequence
<220> FEATURE:
<223> OTHER INFORMATION: RT-PCR forward primer

<400> SEQUENCE: 29
agtggcagca ggaacctcag g                                       21

<210> SEQ ID NO 30
<211> LENGTH: 26
<212> TYPE: DNA
<213> ORGANISM: artificial sequence
<220> FEATURE:
<223> OTHER INFORMATION: RT-PCR reverse primer

<400> SEQUENCE: 30
ggattatatt agggatgaat gagaag                                  26

<210> SEQ ID NO 31
<211> LENGTH: 22
<212> TYPE: DNA
<213> ORGANISM: artificial sequence
<220> FEATURE:
<223> OTHER INFORMATION: RT-PCR forward primer

<400> SEQUENCE: 31
ttaatcagtc tgcacaaggt cg                                      22

<210> SEQ ID NO 32
<211> LENGTH: 25
<212> TYPE: DNA
<213> ORGANISM: RT-PCR reverse primer
<220> FEATURE:
<223> OTHER INFORMATION: amplification primer

| | |
|---|---|
| <400> SEQUENCE: 32 | |
| gggtcattgc aaggattata ttagg | 25 |

<210> SEQ ID NO 33
<211> LENGTH: 1015
<212> TYPE: DNA
<213> ORGANISM: artificial sequence
<220> FEATURE:
<223> OTHER INFORMATION: RT-PCR splice variant product no. 1

| | |
|---|---|
| <400> SEQUENCE: 33 | |
| ttaatcagtc tgcacaaggt cgggttggct gaccccacta atcagcttga | 50 |
| gcctcctaat ccagtggcag caggaacctc aggatgggca gcagtggctt | 100 |
| gtgagagccg gcagggccat tttggccttt ctcctgcaga ctctgtccgg | 150 |
| gaggggatgg ggcagctgag ccatgtrcac caccctcttc ctactcagca | 200 |
| ccttggccat gctctggcgc cgccggttcg ccaaccgggt ccaaccgtga | 250 |
| gaagctgatg gggccatggg cagggatggg gagagaggag aagctagggg | 300 |
| gtgaggggtg gtgcaggggc tgcctggacc tcctgggagg ctggagggcg | 350 |
| gggaggattt gcagggaggt ccagagaggt ttcccatcag agcacgcggg | 400 |
| ggcgggggct cgcaggtgct ccgagactgg ctggagtccc cggtccccca | 450 |
| gcccaacacg gccaggagag ggggttctgg gcccgggcgc tgcccacagc | 500 |
| tcttccagcc tcttcctccc gcccacaggg agcccagcgg agcagacggg | 550 |
| gcagtcgtgg gcagcaggtc ggagagagac ctccagtcct cgggcagaaa | 600 |
| ggaagagcct ctgaagtaag tcttcacccg gtcaggcgga gctcggcccc | 650 |
| agggactggg atcagctggc agaggcagtt caagtcccgg ctggcctctt | 700 |
| acccacaaag catgctgtgg tggaagcagc agcagcagca agaagaaaaa | 750 |
| tgggaaaaag cagtcatcaa gaaggtagac tcctcccttt gagtccctgg | 800 |
| acctgcctgg cctcccttg ccccagaccc tggtggtggg gctcctgaag | 850 |
| caaggcctgg ctggggcagg ctggagggca aagacgctca ttgccctggc | 900 |
| ttgggctccc ttcctctgag atcctgagga tagtctgagg caggcccaga | 950 |
| gagggactca ggtttcttat ggaagggctt ctcattcatc cctaatataa | 1000 |
| tccttgcaat gaccc | 1015 |

<210> SEQ ID NO 34
<211> LENGTH: 733
<212> TYPE: DNA
<213> ORGANISM: artificial sequence
<220> FEATURE:
<223> OTHER INFORMATION: RT-PCR splice variant product no. 2

| | |
|---|---|
| <400> SEQUENCE: 34 | |
| ttaatcagtc tgcacaaggt cgggttggct gaccccacta atcagcttga | 50 |
| gcctcctaat ccagtggcag caggaacctc aggatgggca gcagtggctt | 100 |
| gtgagagccg gcagggccat tttggccttt ctcctgcaga ctctgtccgg | 150 |
| gaggggatgg ggcagctgag ccatgtrcac caccctcttc ctactcagca | 200 |
| ccttggccat gctctggcgc cgccggttcg ccaaccgggt ccaaccggag | 250 |
| cccagcggag cagacggggc agtcgtgggc agcaggtcgg agagagacct | 300 |
| ccagtcctcg ggcagaaagg aagagcctct gaagtaagtc ttcacccggt | 350 |

```
caggcggagc tcggccccag ggactgggat cagctggcag aggcagttca        400
agtcccggct ggcctcttac ccacaaagca tgctgtggtg gaagcagcag        450
cagcagcaag aagaaaaatg ggaaaaagca gtcatcaaga aggtagactc        500
ctccctttga gtccctggac ctgcctggcc tccctttgcc ccagaccctg        550
gtggtggggc tcctgaagca aggcctggct ggggcaggct ggagggcaaa        600
gacgctcatt gccctggctt gggctccctt cctctgagat cctgaggata        650
gtctgaggca ggcccagaga gggactcagg tttcttatgg aagggcttct        700
cattcatccc taatataatc cttgcaatga ccc                          733
```